(12) United States Patent
Matulis et al.

(10) Patent No.: US 12,246,000 B2
(45) Date of Patent: Mar. 11, 2025

(54) INHIBITION OF PROTEIN AMYLOID AGGREGATION USING FLUORINATED BENZENESULFONAMIDES

(71) Applicant: Vilnius University, Vilnius (LT)

(72) Inventors: Daumantas Matulis, Vilnius (LT); Andrius Sakalauskas, Vilnius (LT); Virginija Dudutiene, Vilnius (LT); Mantas Zvirblis, Vilnius (LT); Mantas Ziaunys, Vilnius (LT); Vytautas Smirnovas, Vilnius (LT)

(73) Assignee: Vilnius University, Vilnius (LT)

( * ) Notice: Subject to any disclaimer, the term of this patent is extended or adjusted under 35 U.S.C. 154(b) by 14 days.

(21) Appl. No.: 17/948,251

(22) Filed: Sep. 20, 2022

(65) Prior Publication Data
US 2024/0000736 A1    Jan. 4, 2024

(30) Foreign Application Priority Data
Jun. 30, 2022  (EP) .................................... 22182182

(51) Int. Cl.
*A61K 31/196*  (2006.01)
*A61K 31/18*   (2006.01)
(Continued)

(52) U.S. Cl.
CPC ............ *A61K 31/196* (2013.01); *A61K 31/18* (2013.01); *A61K 31/195* (2013.01); *A61K 31/63* (2013.01); *A61P 25/28* (2018.01)

(58) Field of Classification Search
CPC .............................. A61K 31/196; A61P 25/28
See application file for complete search history.

(56) References Cited

U.S. PATENT DOCUMENTS 7,858,658 B2    12/2010  Kreft et al.
9,725,467 B2 *   8/2017  Matulis ................. C07C 317/18
(Continued)

FOREIGN PATENT DOCUMENTS

WO    2006118959 A3    11/2006

OTHER PUBLICATIONS

Singh, P., Mishra, G., Dinda, S.C. (2021). Natural Excipients in Pharmaceutical Formulations. In: Mandal, S.C., Chakraborty, R., Sen, S. (eds) Evidence Based Validation of Traditional Medicines. Springer, Singapore. (Year: 2021).*

(Continued)

*Primary Examiner* — John S Kenyon
*Assistant Examiner* — John D McAnany
(74) *Attorney, Agent, or Firm* — Koivula & Somersalo, LLC

(57) ABSTRACT

This invention teaches a class of fluorinated benzensulfonamides of general structure I, as shown:

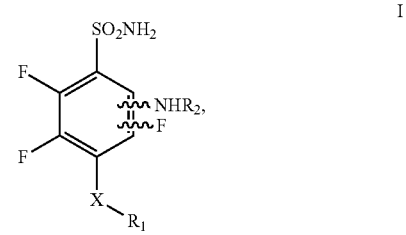

which are useful for inhibiting protein amyloid aggregation. The compounds taught can be used in pharma-
(Continued)

ceutical compositions in effective amounts to treat illnesses that result from protein amyloid aggregation.

10 Claims, 5 Drawing Sheets

(51) Int. Cl.
*A61K 31/195* (2006.01)
*A61K 31/63* (2006.01)
*A61P 25/28* (2006.01)

(56) References Cited

U.S. PATENT DOCUMENTS

2011/0071199 A1  3/2011  Starrett
2013/0261045 A1  10/2013  Shytle et al.

OTHER PUBLICATIONS

Giorgetti, S.; Greco, C.; et al. "Targeting Amyloid Aggregation: An Overview of Strategies and Mechanisms" Int. J. Mol. Sci. 2018, 19, 2677 (Year: 2018).*
Patani, G. A.; LaVoie, E. J. "Bioisosterism: A Rational Approach in Drug Design" Chem. Rev. 1996, 96, 3147-3176. (Year: 1996).*
Merlini, G. et al. "Amyloidosis: pathogenesis and new therapeutic options", J. Clin. Oncol. 29, 1924-1933 (2011).
Knowles, T. P. et al. "The amyloid state and its association with protein misfolding diseases", Nat. Rev. Mol. Cell Biol. 15, 384-396 (2014).
Yiannopoulou, K. G. and Papageorgiou, S. G. "Current and Future Treatments in Alzheimer Disease: An Update", J. Cent. Nerv. Syst. Dis. 12, 117957352090739 (2020).
Cummings, J. et al. "Alzheimer's disease drug development pipeline: 2020", Alzheimer's Dement. Transl. Res. Clin. Interv. 6, e12050 (2020).
Phan, H. T. T. et al. "Polyphenols Modulate Alzheimer's Amyloid Beta Aggregation in a Structure-Dependent Manner", Nutrients, 11(4), 756 (2019).
Hortschansky, P. et al. "The aggregation kinetics of Alzheimer's beta-amyloid peptide is controlled by stochastic nucleation", Protein Sci. 14, 1753-1759 (2005).
Brännström, K. et al. "The Properties of Amyloid-β Fibrils are Determined by their Path of Formation", J. Mol. Biol. 430, 1940-1949 (2018).
Gazit, "Self Assembly of Short Aromatic Peptides into Amyloid Fibrils and Related Nanostructures", E. Prion 1, 32-35 (2007).
Kumar, S. et al. "Antibacterial activities of sulfonyl or sulfonamide containing heterocyclic derivatives and its structure-activity relationships (SAR) studies: A critical review", Bioorg. Chem. 105, 104400 (2020).
Supuran, C. T et al. "Antiviral sulfonamide derivatives", Mini-Rev. Med. Chem. 4, 189-200 (2004).
Oudah, K. H. et al. "The Recent Progress of Sulfonamide in Medicinal Chemistry." Syst. Rev. Pharm. 11, 1473-1477 (2020).
Bag, S. et al. "Sulfonamides as multifunctional agents for Alzheimer's disease", Bioorganic Med. Chem. Lett. 25, 626-630 (2014).
Kurnik, M. et al. "Potent a-Synuclein Aggregation Inhibitors, Identified by High-Throughput Screening, Mainly Target the Monomeric State", Cell Chem. Biol. 25, 1389-1402.e9 (2018).
Dudutienė, V. et al. "4-Substituted-2,3,5,6-tetrafluorobenzenesulfonamides as inhibitors of carbonic anhydrases I, II, VII, XII, and XIII", Bioorg. Med. Chem. 21, 2093-2106 (2013).
Dudutienė, V. et al. ChemMedChem 10, 662-687 (2015).
Kazokaitė, J. et al. "Novel fluorinated carbonic anhydrase IX inhibitors reduce hypoxia-induced acidification and clonogenic survival of cancer cells", Oncotarget, 9(42),: 26800-26816 (2018).
Šneideris, T. et al. "Looking for a generic inhibitor of amyloid-like fibril formation among flavone derivatives", Peer J. 3: e1271 (2015).
Baker K.R.,and Rice L The amyloidoses: clinical features, diagnosis and treatment. Methodist Debakey Cardiovasc. J. 8 (3), 3-7 (2012).

* cited by examiner

INHIBITION OF PROTEIN AMYLOID AGGREGATION USING FLUORINATED BENZENESULFONAMIDES

CROSS-REFERENCE TO RELATED APPLICATION

This patent application claims the benefit of an earlier filed foreign application, EP 22182182.0 filed Jun. 30, 2022. The above applications are incorporated by reference herein.

FIELD OF THE INVENTION

This invention provides compounds for prevention and/or treatment of diseases related to protein amyloid aggregation. This invention relates to compounds-fluorinated benzensulfonamides, which are useful for inhibiting protein amyloid aggregation.

BACKGROUND OF THE INVENTION

Amyloidogenic protein association into insoluble fibrillar aggregates is linked with the onset and progression of several amyloidoses (Merlini, G. et al. *J. Clin. Oncol.* 29, 1924-1933 (2011); Baker, K. R. and Rice, L. *Methodist Debakey Cardiovasc. J.* 8 (3), 3-7 (2012)). Currently, there are over 30 known amyloidogenic proteins, which can form these fibrillar structures. Several of them are linked to degenerative disorders, such as Alzheimer's disease (amyloid-beta peptide, Tau protein), Parkinson's disease (alpha-synuclein), spongiform encephalopathies (prion protein), type 2 diabetes (islet amyloid polypeptide), amyotrophic lateral sclerosis (superoxide dismutase 1) (Knowles, T. P. et al. *Nat. Rev. Mol. Cell Biol.* 15, 384-396 (2014)). The incidence of these amyloid-related disorders is in the tens of millions and is projected to increase even further (Brookmeyer, R. et al. *Am. J. Public Health* 88, 1337-1342 (1998); Arthur, K. C. et al. *Nat. Commun.* 7, 12408 (2016)), due to the continuous rise of the average human lifespan (Kontis, V. et al. *Lancet* 389, 1323-1335 (2017)). Despite such a large prevalence and impact on the health of an aging society, countless studies have yet to produce an effective, disease-modulating, or inhibiting compound/treatment (Yiannopoulou, K. G. and Papageorgiou, S. G. *J. Cent. Nerv. Syst. Dis.* 12, 117957352090739 (2020)). Currently, clinical trials are being conducted on more than one hundred potential drugs, which range from simple molecular structure compounds, such as polyphenols/flavonoids (U.S. Pat. No. 9,463,195 (B2)), to complex monoclonal antibodies or compound mixtures (Cummings, J. et al. *Alzheimer's Dement. Transl. Res. Clin. Interv.* 6, e12050 (2020)). They have shown the ability to inhibit amyloid formation by either directly targeting amyloidogenic proteins (Phan, H. T. T. et al. *Nutrients*, 11(4), 756 (2019); WO 2006118959 (A3)), or inhibiting their production (US 2013261045 (A1)). However, in the case of the most widespread neurodegenerative disorders, clinical trials keep failing at different stages and there is still no effective cure available (Mehta, D. et al. *Expert Opin. Investig. Drugs* 26, 735-739 (2017)). This is, in part, due to the complex nature of amyloid aggregation (Hortschansky, P. et al. *Protein Sci.* 14, 1753-1759 (2005)) which encompasses several steps of formation/propagation (Brännström, K. et al. *J. Mol. Biol.* 430, 1940-1949 (2018); Petkova, A. T. et al. *Science*, 307, 262-265 (2005)) and because the environment has a large impact on their effectiveness (Morel, B. et al. *Biophys. J.* 99, 3801-3810 (2010); Sneideris, T. et al. *Biomolecules* 9 (12), 855 (2019)). This means that drugs, which show great promise in vitro, can be completely ineffective under physiological conditions.

Amyloid aggregation is a process composed of three main phases. The first one is the assembly of a nucleus (primary nucleation), during which active protein molecules aggregate into a beta-sheet rich structure (Lee, C. T. and Terentjev, E. M. *J. Chem. Phys.* 147, 105103 (2017)). Once a stable nucleus forms, it is then capable of incorporating other homologous protein molecules into its structure, thus elongating the aggregate into a fibril (elongation) (Gurry, T. and Stultz, C. M. *Biochemistry* 53, 6981-6991 (2014)). Once a sufficient size aggregate forms, it can fragment and create additional fibril ends (fragmentation) or new nuclei can form on their surface, which acts as a catalyst via surface-mediated nucleation (Meisl, G. et al. *Proc. Natl. Acad. Sci.* 111, 9384-9389 (2014); Scheidt, T. et al. *Sci. Adv.* 5, eaau3112 (2019)). These processes result in exponential aggregate formation. Finally, once all nearby aggregation-capable protein molecules are in their aggregated-state, the process slows down or completely stops.

A compound which affects the nucleation step could potentially be used as a preventative measure for amyloid related disorders because a stable nucleus is required to initiate the exponential phase of aggregate accumulation. Nucleation-inhibition could also work at later stages of these diseases, when fibrillar structures are already present, by inhibiting fibril-enhanced nucleation. Ideally, in vitro inhibition should also show potential at physiological or near-physiological conditions to ensure the possibility of the effect persisting in vivo as well. Considering that amyloid aggregation can occur for a wide range of proteins and there is no specific amino acid sequence or peptide-length required (Gazit, E. *Prion* 1, 32-35 (2007)), it is extremely difficult to predict what type of compounds will affect which protein's aggregation. In a perfect scenario, the drug molecule should also prevent the formation of highly distinct protein fibrils, i.e., have a universal effect on amyloid-formation.

Compounds containing a sulfonamide group have a long history and a wide range of medicinal applications, ranging from anti-bacterial (Kumar, S. et al. *Bioorg. Chem.* 105, 104400 (2020)) to anti-viral (Supuran, C. T et al. *Mini-Rev. Med. Chem.* 4, 189-200 (2004)) drugs. Among the thousands of sulfonamide derivatives, new potential drugs or compounds with comparatively higher effectiveness are continuously being discovered (Oudah, K. H. et al. *Syst. Rev. Pharm.* 11, 1473-1477 (2020)). In recent years, sulfonamides have been shown to have anti-amyloid properties (Bag, S. et al. *Bioorganic Med. Chem. Lett.* 25, 626-630 (2015)) against some of the most prevalent neurodegenerative disease-related proteins and peptides (alpha-synuclein (Kurnik, M. et al. *Cell Chem. Biol.* 25, 1389-1402.e9 (2018)) and amyloid beta (Shuaib, S. and Goyal, B. *J. Biomol. Struct. Dyn.* 36, 663-678 (2018); U.S. Pat. No. 7,858,658B2; US20110071199A1). Therefore, sulfonamide-based compounds can be compounds of interest searching for a new treatment against neurogenerative disease-related protein aggregation.

SUMMARY OF THE INVENTION

The present invention aims to provide compounds for prevention and/or treatment of diseases related to protein amyloid aggregation. In the present disclosure, fluorinated benzensulfonamides were found useful for inhibiting protein amyloid aggregation. These compounds are effective as inhibitors of beta-amyloid aggregation and can be applied for inhibition of the amyloid aggregation process occurring in any amyloidogenic protein from the group of: beta amyloid peptide, alpha-synuclein, prion protein, Tau protein, superoxide dismutase 1, islet amyloid polypeptide, insulin, and lysozyme. The pharmacological action of these compounds makes them useful for treating conditions responsive to the inhibition of protein amyloid aggregation; e.g., Alzheimer's disease, Parkinson's disease, Dementia with Lewy bodies, Multiple system atrophy, Creutzfeldt-Jakob disease, Fatal insomnia, Gerstmann-Straussler-Scheinker disease, Huntington disease and other diseases, including signs and/or symptoms related to said diseases.

DETAILED DESCRIPTION OF THE INVENTION

Figure 1:
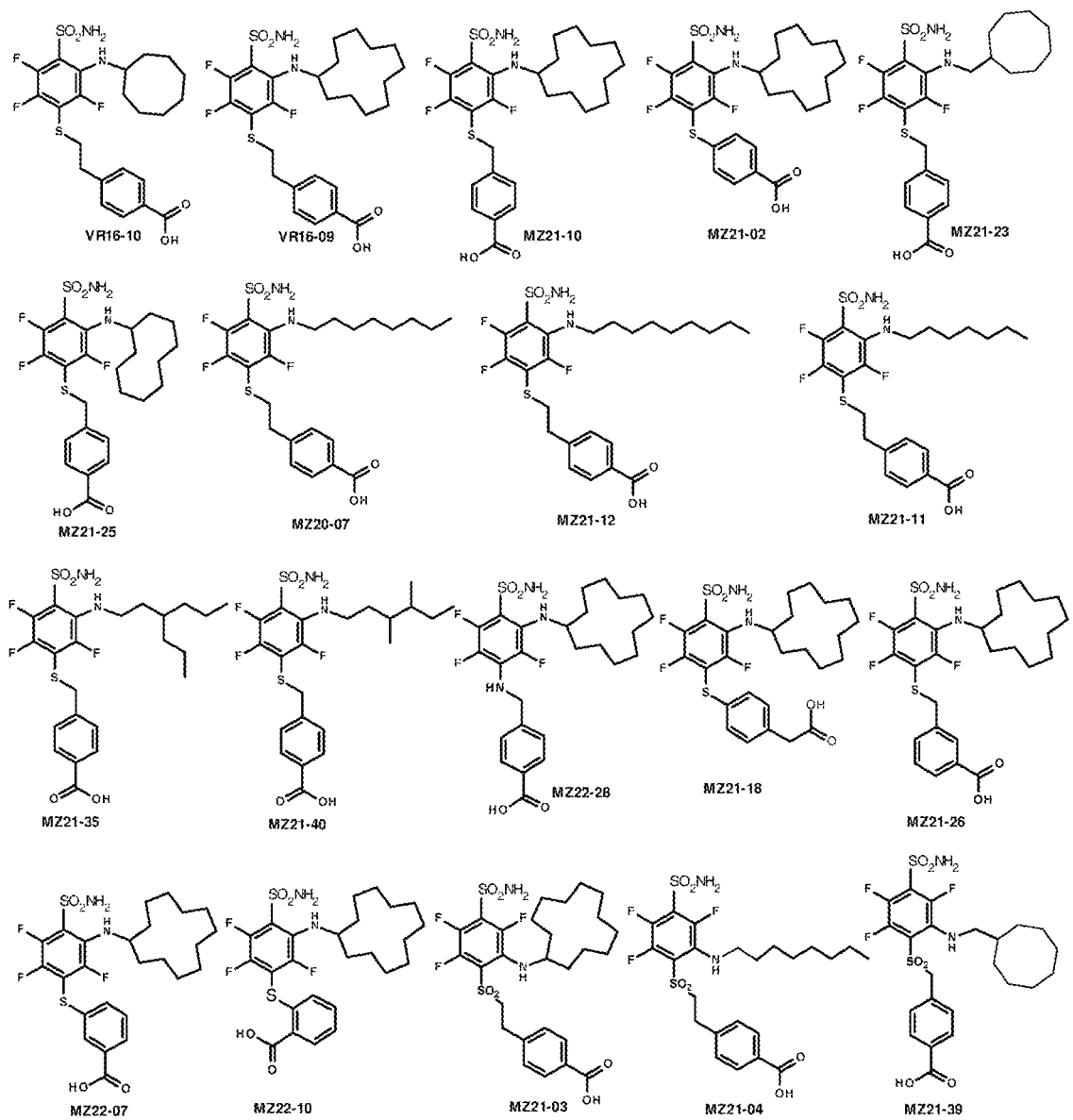
FIG. 1 shows chemical structures of selected inhibitors of amyloid aggregation.
Figure 2:
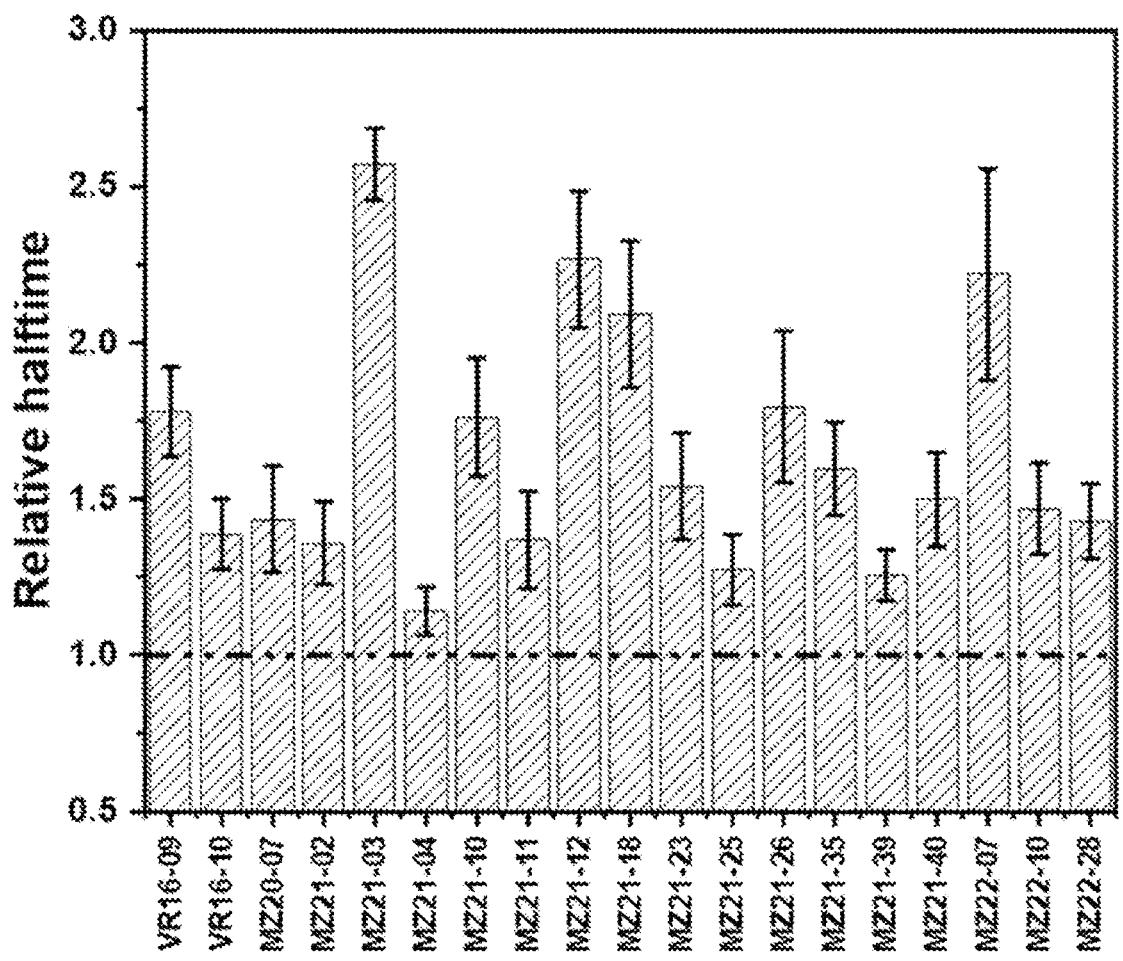
FIG. 2 shows amyloid-beta aggregation relative halftime values when the reaction takes place in the presence of sulfonamide derivatives. Values for each condition were determined by dividing the aggregation halftime values in the presence of sulfonamide derivatives by the control values (n=4 for each condition).
Figure 3A:
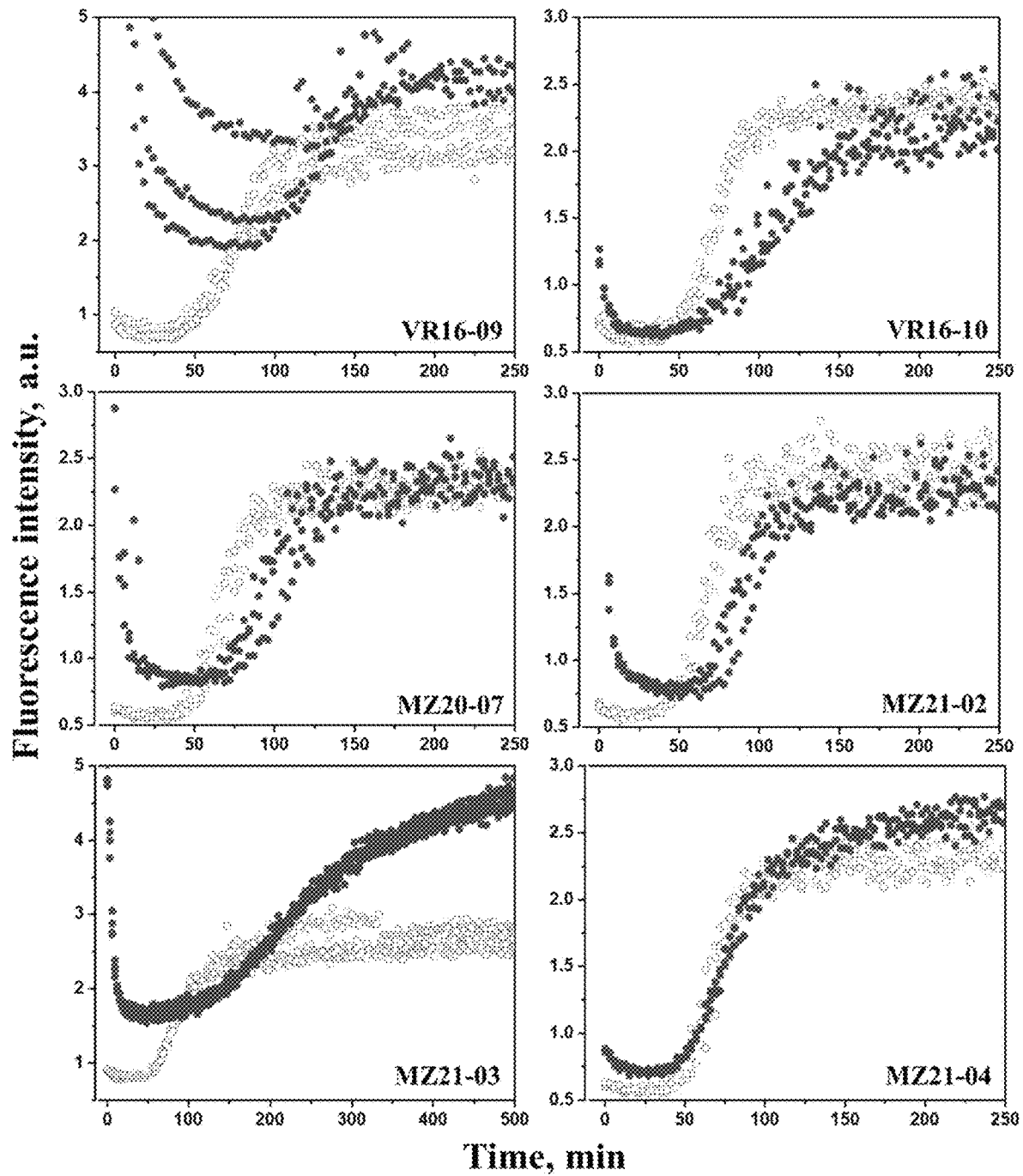
FIGS. 3A-3C show amyloid-beta aggregation kinetic curves in the presence of inhibiting compounds (name code in the bottom-right of each graph). Three independent kinetic curves of the control sample (open circles) and the sample with selected compound (solid circles) are displayed in each graph.
Figure 3B:
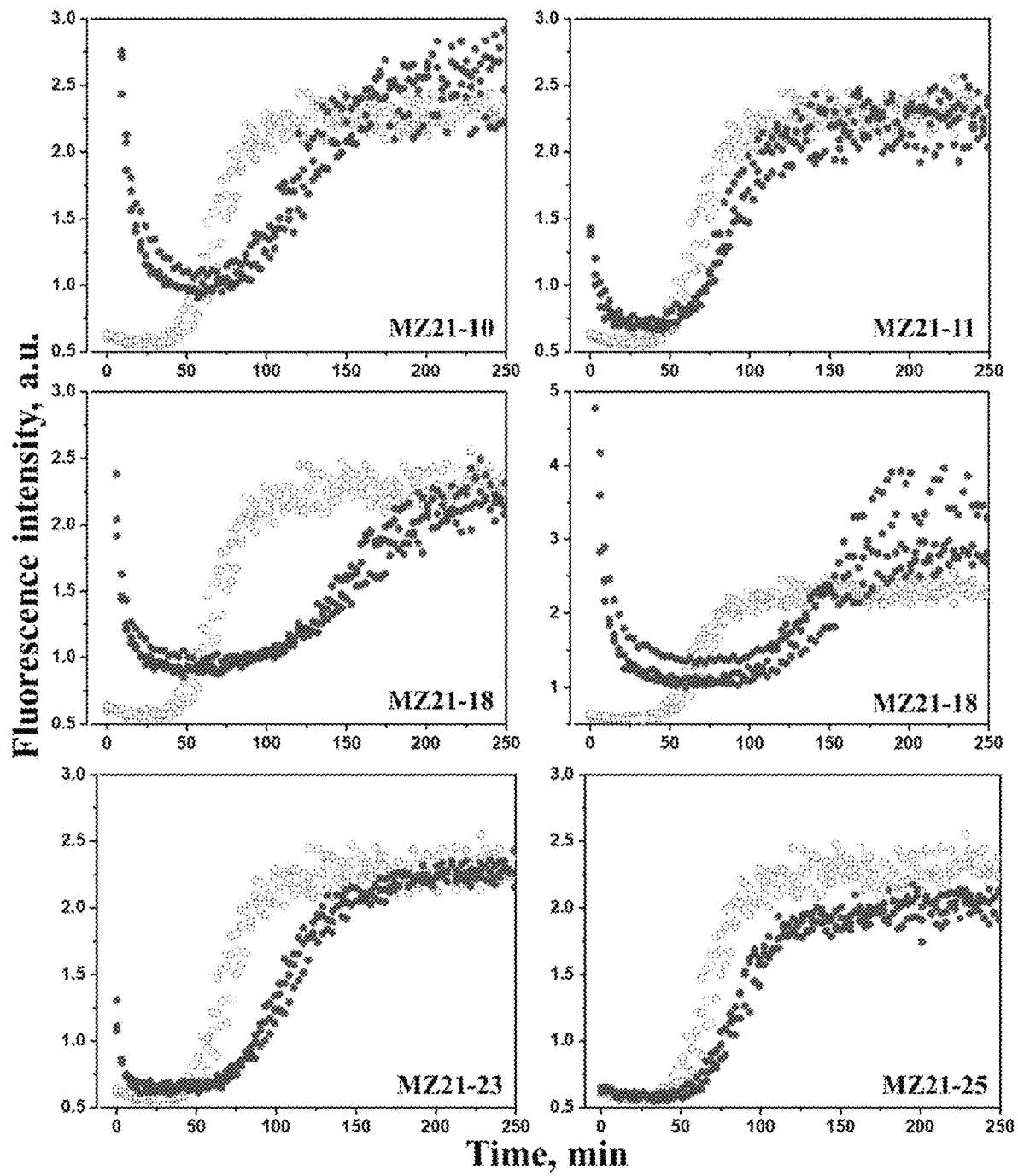
Figure 3C:
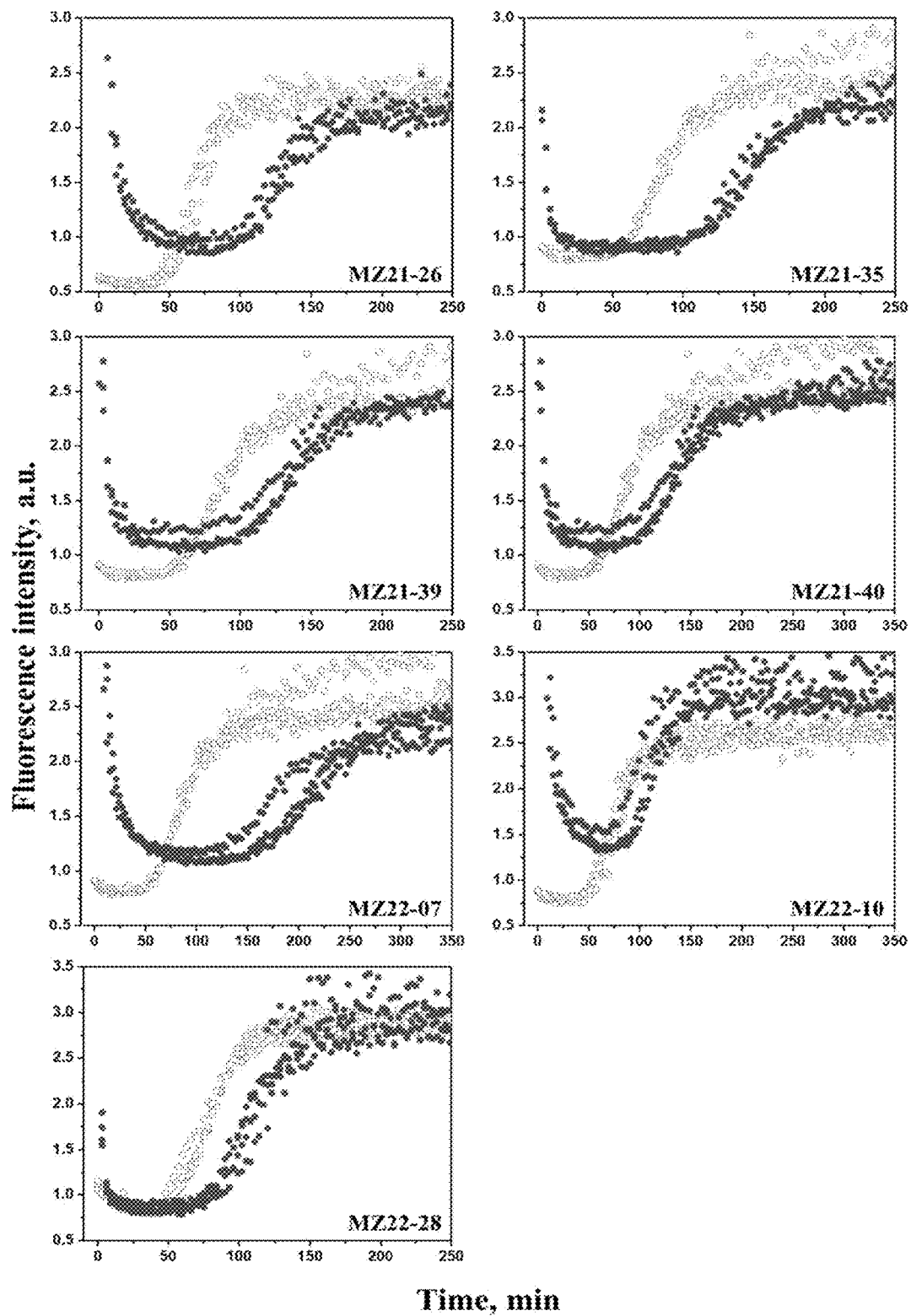

Pharmaceutical compositions comprising fluorinated benzenesulfonamides are taught herein for the inhibition of protein amyloid aggregation. The pharmaceutical compositions of the invention are also the non-toxic, pharmaceutically acceptable salts of the benzenesulfonamides. The compositions include all salts which retain activity comparable to original compounds and do not attain any harmful and undesirable effects.

The compounds based on fluorinated benzenesulfonamide structure for treatment of illnesses related to amyloid aggregation. Fluorinated benzenesulfonamides having a general structural formula I are taught herein.

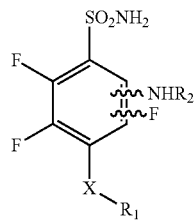

I wherein X is S, NH, or SO$_2$;

NHR$_2$ and F are at ortho and meta positions with respect to the sulfonamide group, such that when X=S or NH, NHR$_2$ is at ortho position and F is at meta position, and when X=SO$_2$, NHR$_2$ is at meta position and F is at ortho position.

R$_1$ is selected from the group consisting of:

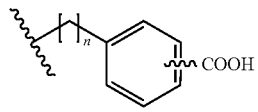

where n=0, 1, or 2, and COOH is at the position ortho, meta, or para, as shown:

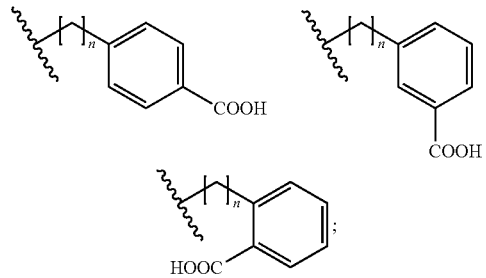

benzene-dicarboxylic acid where n=0, 1, or 2, and COOH groups are at different positions of benzene ring, as shown:

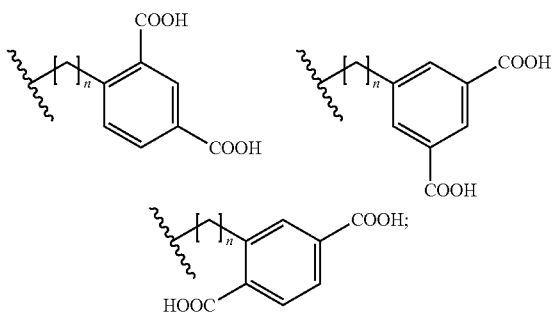

2-phenylacetic acid, as shown:

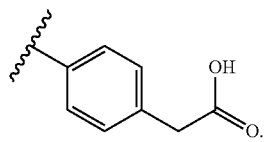 [SMILES: *c1ccc(CC(=O)O)cc1]

R$_2$ is cycloalkyl where cycloalkyl comprises cycloalkanes from cyclooctane to cyclotetradecane (C8-C14);
cycloalkylmethyl where cycloalkyl comprises cycloalkanes from cyclohexane to cyclododecane (C6-C12);
alkyl where alkyl comprises alkanes from hexane to tetradecane (C6-C14); or
alkyl where alkyl comprises various structures of branched alkanes from C6 to C14 (the total number of carbon atoms of branched alkanes).

Examples of branched alkanes from C6 to C14 are given but not restricted to the following: 3,4-dimethylhexylamine, 3,4-dimethylheptylamine, 1-methylheptylamine, 1-ethylheptylamine, 1-propylheptylamine, 4-methylheptylamine, 3-methylheptylamine, 2-methylheptylamine, 6-methylheptylamine, 5-methylheptylamine, 5-ethylheptylamine, 2,2-dimethylheptylamine, 3,3-dimethylheptylamine, 2,6-dimethylheptylamine, 6,6-dimethylheptylamine, 5,5-dimethylheptylamine, 3,3,6-trimethylheptylamine, 3,3,5-trimethylheptylamine, 3,3,4-trimethylheptylamine, 2,4,6-trimethylheptylamine, 4,6,6-trimethylheptylamine, 2,6,6-trimethylheptylamine, 2,2,6-trimethylheptylamine, 2,2,4-trimethylheptylamine, 5,6,6-trimethylheptylamine, 5,5,6-trimethylheptylamine, 3,6,6-trimethylheptylamine, 3,5,5-trimethylheptylamine, 5-ethyl-6-methylheptylamine, 5-ethyl-4-methylheptylamine, 5-ethyl-3-methylheptylamine, 3-ethyl-6-methylheptylamine, 3-ethyl-5-methylheptylamine, 3-ethyl-4-methylheptylamine, 2-ethyl-6-methylheptylamine, 1-methyloctylamine, 1-ethyloctylamine, 5-methyloctylamine, 3-ethyloctylamine, 4-ethyloctylamine, 6-ethyloctylamine, 6-methyloctylamine, 7-methyloctylamine, 3,7-dimethyloctylamine, 2,7-dimethyloctylamine, 4,6-dimethyloctylamine, 4,7-dimethyloctylamine, 7,7-dimethyloctylamine, 3,3-dimethyloctylamine, 6,6-dimethyloctylamine, 2-methylnonylamine, 8-methylnonylamine, 5-methylnonylamine, 4-methylnonylamine, and 1-methylnonylamine.

The compounds based on fluorinated benzensulfonamide structure for treatment of illnesses related to amyloid aggregation. Compound having general structure I, wherein the compound is of formula Ia or a salt thereof.

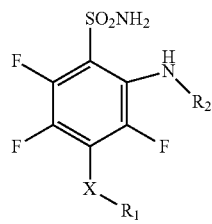

Ia wherein X is S or NH;
$R_1$ is selected from the group consisting of:

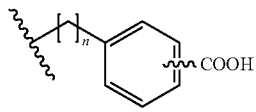

where n=0, 1, or 2, and COOH is at the position ortho, meta, or para, as shown:

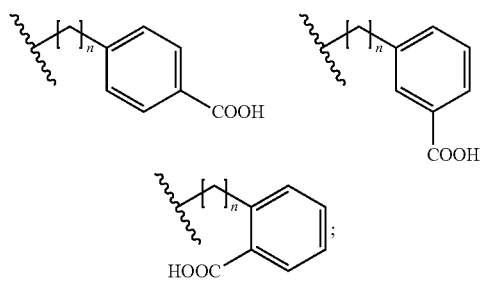

benzene-dicarboxylic acid where n=0, 1, or 2, and COOH groups are at different positions of benzene ring, as shown:

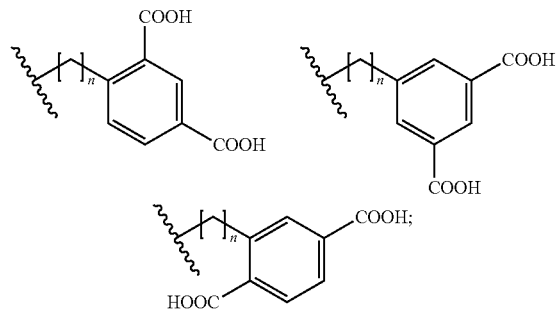

2-phenylacetic acid, as shown:

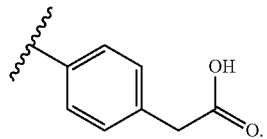 [SMILES: *c1ccc(CC(=O)O)cc1]

$R_2$ is cycloalkyl where cycloalkyl comprises cycloalkanes from cyclooctane to cyclotetradecane (C8-C14);

cycloalkylmethyl where cycloalkyl comprises cycloalkanes from cyclohexane to cyclododecane (C6-C12);

alkyl where alkyl comprises alkanes from hexane to tetradecane (C6-C14); or alkyl where alkyl comprises various structures of branched alkanes from C6 to C14 (the total number of carbon atoms of branched alkanes).

Examples of branched alkanes from C6 to C14 are given but not restricted to the following list: 3,4-dimethylhexylamine, 3,4-dimethylheptylamine, 1-methylheptylamine, 1-ethylheptylamine, 1-propylheptylamine, 4-methylheptylamine, 3-methylheptylamine, 2-methylheptylamine, 6-methylheptylamine, 5-methylheptylamine, 5-ethylheptylamine, 2,2-dimethylheptylamine, 3,3-dimethylheptylamine, 2,6-dimethylheptylamine, 6,6-dimethylheptylamine, 5,5-dimethylheptylamine, 3,3,6-trimethylheptylamine, 3,3,5-trimethylheptylamine, 3,3,4-trimethylheptylamine, 2,4,6-trimethylheptylamine, 4,6,6-trimethylheptylamine, 2,6,6-trimethylheptylamine, 2,2,6-trimethylheptylamine, 2,2,4-trimethylheptylamine, 5,6,6-trimethylheptylamine, 5,5,6-trimethylheptylamine, 3,6,6-trimethylheptylamine, 3,5,5-trimethylheptylamine, 5-ethyl-6-methylheptylamine, 5-ethyl-4-methylheptylamine, 5-ethyl-3-methylheptylamine; 3-ethyl-6-methylheptylamine, 3-ethyl-5-methylheptylamine, 3-ethyl-4-methylheptylamine, 2-ethyl-6-methylheptylamine, 1-methyloctylamine, 1-ethyloctylamine, 5-methyloctylamine, 3-ethyloctylamine, 4-ethyloctylamine, 6-ethyloctylamine, 6-methyloctylamine, 7-methyloctylamine, 3,7-dimethyloctylamine, 2,7-dimethyloctylamine, 4,6-dimethyloctylamine, 4,7-dimethyloctylamine, 7,7-dimethyloctylamine, 3,3-dimethyloctylamine, 6,6-dimethyloctylamine, 2-methylnonylamine, 8-methylnonylamine, 5-methylnonylamine, 4-methylnonylamine, and 1-methylnonylamine.

The compounds based on fluorinated benzensulfonamide structure for treatment of illnesses related to amyloid aggregation. Compound having general structure I, wherein the compound is of formula Ib or a salt thereof

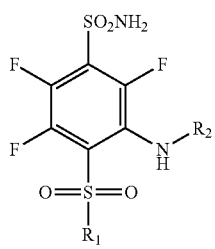

R₁ is selected from the group consisting of:

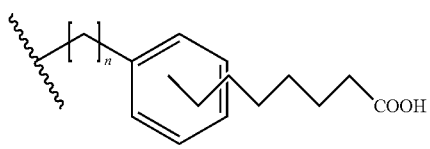

where n=0, 1, or 2, and COOH are at positions ortho, meta, or para, as shown:

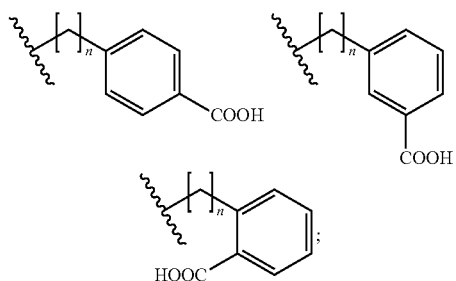

benzene-dicarboxylic acid where n=0, 1, or 2, and COOH groups are at different positions of benzene ring, as shown:

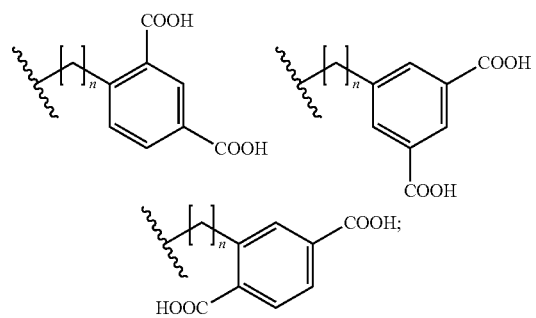

2-(4-sulfanylphenyl)acetic acid, as shown:

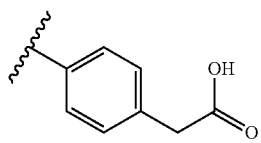 [SMILES: *c1ccc(CC(=O)O)cc1]

R₂ is cycloalkyl where cycloalkyl comprises cycloalkanes from cyclooctane to cyclotetradecane (C8-C14); cycloalkylmethyl where cycloalkyl comprises cycloalkanes from cyclohexane to cyclododecane (C6-C12);

alkyl where alkyl comprises alkanes from hexane to tetradecane (C6-C14); or alkyl where alkyl comprises various structures of branched alkanes from C6 to C14 (the total number of carbon atoms of branched alkanes).

Examples of branched alkanes from C6 to C14 are given but not restricted to the following: 3,4-dimethylhexylamine, 3,4-dimethylheptylamine, 1-methylheptylamine, 1-ethylheptylamine, 1-propylheptylamine, 4-methylheptylamine, 3-methylheptylamine, 2-methylheptylamine, 6-methylheptylamine, 5-methylheptylamine, 5-ethylheptylamine, 2,2-dimethylheptylamine, 3,3-dimethylheptylamine, 2,6-dimethylheptylamine, 6,6-dimethylheptylamine, 5,5-dimethylheptylamine, 3,3,6-trimethylheptylamine, 3,3,5-trimethylheptylamine, 3,3,4-trimethylheptylamine, 2,4,6-trimethylheptylamine, 4,6,6-trimethylheptylamine, 2,6,6-trimethylheptylamine, 2,2,6-trimethylheptylamine, 2,2,4-trimethylheptylamine, 5,6,6-trimethylheptylamine, 5,5,6-trimethylheptylamine, 3,6,6-trimethylheptylamine, 3,5,5-trimethylheptylamine, 5-ethyl-6-methylheptylamine, 5-ethyl-4-methylheptylamine, 5-ethyl-3-methylheptylamine; 3-ethyl-6-methylheptylamine, 3-ethyl-5-methylheptylamine, 3-ethyl-4-methylheptylamine, 2-ethyl-6-methylheptylamine, 1-methyloctylamine, 1-ethyloctylamine, 5-methyloctylamine, 3-ethyloctylamine, 4-ethyloctylamine, 6-ethyloctylamine, 6-methyloctylamine, 7-methyloctylamine, 3,7-dimethyloctylamine, 2,7-dimethyloctylamine, 4,6-dimethyloctylamine, 4,7-dimethyloctylamine, 7,7-dimethyloctylamine, 3,3-dimethyloctylamine, 6,6-dimethyloctylamine, 2-methylnonylamine, 8-methylnonylamine, 5-methylnonylamine, 4-methylnonylamine, and 1-methylnonylamine.

Compounds taught by structures Ia and Ib can be used in pharmaceutical compositions and administered with pharmaceutically acceptable diluents, excipient or carrier for the treatment of illnesses caused by amyloid aggregation. In particular, said pharmaceutical compositions comprising the taught fluorinated benzenesulfonamide compounds inhibit amyloid aggregation process in any amyloidogenic protein such as beta amyloid peptide, alpha-synuclein, prion protein, Tau protein, superoxide dismutase 1, islet amyloid polypeptide, insulin or lysozyme.

Exemplary uses of pharmaceutical compositions comprising compounds taught by structures Ia and Ib include control of conditions where inhibition of amyloid aggregation is necessary. Such conditions include Alzheimer's disease, Hereditary cerebral hemorrhage with amyloidosis, Parkinson's disease, Dementia with Lewy bodies, Multiple system atrophy, Creutzfeldt-Jakob disease, Fatal insomnia, Gerstmann-Straussler-Scheinker disease, Huntington disease, Spongiform encephalopathy, New variant Creutzfeldt-Jakob disease, Kuru, Hereditary sensory and autonomic neuropathy, Pick disease, Progressive supranuclear palsy, Corticobasal degeneration, Frontotemporal dementia, Argyrophilic grain disease, Tangle predominant dementia, Guam Parkinson dementia complex, Frontotemporal lobar degeneration, Chronic traumatic encephalopathy, Ganglioglioma, Meningioangiomatosis, Subacute sclerosing panencephalitis, Lead encephalopathy, Tuberous sclerosis, Hallervorden-Spatz disease, Lipofuscinosis, Familial British dementia, Familial Danish dementia, Light-chain amyloidosis, Heavy-chain amyloidosis, AA amyloidosis, Senile systemic amyloidosis, Familial amyloidotic polyneuropathy, Familial amyloid cardiomyopathy, Leptomeningeal amyloidosis, Dialysis-related amyloidosis, ApoAI amyloidosis, ApoAII amyloidosis, ApoAIV amyloidosis, ApoCII amyloidosis, ApoCIII amyloidosis, Familial amyloidosis (Finnish type), Lysozyme amyloidosis, Fibrinogen amyloidosis, Hereditary cerebral hemorrhage with amyloidosis, Type II diabetes, Insulinoma, Medullary carcinoma of the thyroid, Atrial amyloidosis, Pituitary prolactinoma, Injection-localized amyloidosis, Aortic medial amyloidosis, Gelatinous drop-like corneal dystrophy, Calcifying epithelial odontogenic tumors, Pulmonary alveolar proteinosis, Renal amyloidosis, Lichen amyloidosus, Macular amyloidosis, Hypotrichosis simplex of the scalp, Lattice corneal dystrophy (type 1), Lattice corneal dystrophy (type 3A), Lattice corneal dystrophy (Avellino type), Seminal vesicle amyloidosis, Prostate cancer, including signs and/or symptoms related to said diseases.

General Reaction Schemes

The compounds of the invention can be obtained according to general synthesis schemes A, B.

A series of compounds bearing fluorinated benzensulfonamide scaffold were invented. First series include compounds bearing substituents at para and ortho positions according to sulfonamide group (Scheme A). Different routes of synthesis were proceeded for compounds bearing sulfur-centered or nitrogen-centered nucleophiles at the para position. The first stage is similar for both routes. Pentafluorobenzenesulfonyl chloride (Acros Organics) was converted to pentafluorobenzenesulfonamide via amination with aqueous ammonia according to a procedure described previously (Dudutienė, V. et al. Bioorg. Med. Chem. 21, 2093-2106 (2013)). Following aromatic nucleophilic substitution reaction using sulfur-centered nucleophiles in solvent such as MeOH, substitution preferentially occurred at the para position, and the reaction was proceeded using the previously described method (Dudutienė, V. et al. Bioorg. Med. Chem. 21, 2093-2106 (2013); U.S. Pat. No. 9,725,467 (B2); EP2914583(B1)). Reactions can be carried out with sulfur-centered nucleophiles bearing carboxylic acid substituent. The aromatic nucleophilic substitution reaction with nitrogen-centered nucleophiles in solvent such as benzene preferentially occurred at an ortho position, and the reaction was proceeded using the previously described method (Dudutienė, V. et al. ChemMedChem 10, 662-687 (2015)). Nitrogen-centered nucleophiles are based on hydrophobic, aliphatic core structure, which include linear alkanes or branched alkanes, cycloalkanes, and methylcycloalkanes. The second aromatic nucleophilic substitution reaction of compounds already bearing sulfur substituent at the para position was carried out with nitrogen-centered nucleophiles according to methodology previously described (Dudutienė, V. et al. ChemMedChem 10, 662-687 (2015); U.S. Pat. No. 9,725,467 (B2); EP2914583(B1)). Nitrogen-centered nucleophiles are based on hydrophobic, aliphatic core structure including linear alkanes or branched alkanes, cycloalkanes, and methylcycloalkanes. The second aromatic nucleophilic substitution reaction of compounds already bearing hydrophobic nitrogen substituent at an ortho position was carried out with nitrogen-centered nucleophiles possessing carboxylic acid substituent or masked carboxylic acid as a carboxylic acid ester substituent.

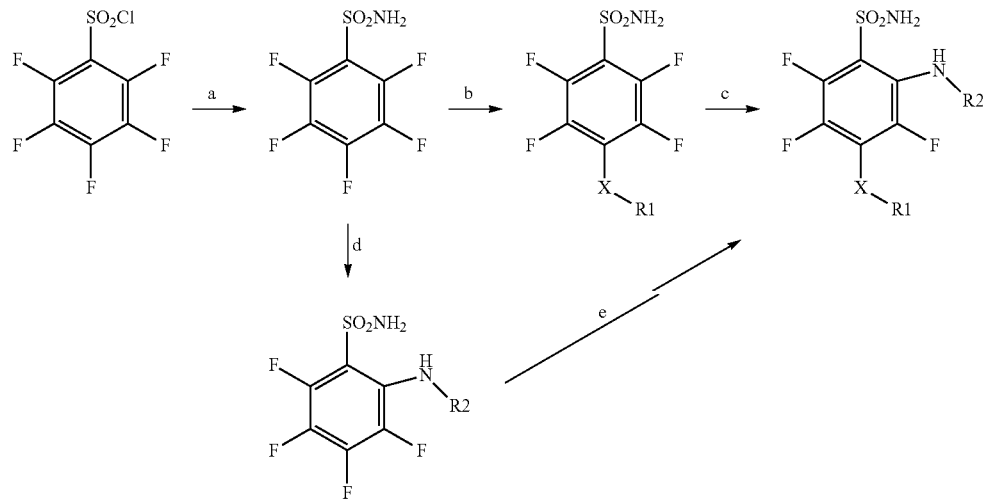

Scheme A. Synthesis of ortho and para substituted compounds. Reagents: a) aq NH$_3$, THF; b) 1) HSR$_1$, Et$_3$N, MeOH; 2) conc. HCl; c) 1) NH$_2$R$_2$, Et$_3$N, DMSO; 2) H$_2$O, HCl; d) NH$_2$R$_2$, Et$_3$N, C$_6$H$_6$; e) 1) NH$_2$R$_1$, Et$_3$N, DMSO.

Second series include compounds bearing substituents at para and meta positions according to sulfonamide group (Scheme B). The aromatic nucleophilic substitution reaction at para position was proceeded using the previously described method (Dudutienė, V. et al. Bioorg. Med. Chem. 21, 2093-2106 (2013); U.S. Pat. No. 9,725,467 (B32); EP2914583(B1)). Reactions can be carried out with sulfur-centered nucleophiles bearing carboxylic acid substituent. Sulfur-containing compounds were oxidized and fluorine substituent at meta position became susceptible to aromatic nucleophilic substitution reaction. The second aromatic nucleophilic substitution reaction with nitrogen-centered nucleophiles was carried out according to methodology previously described (Dudutienė, V. et al. ChemMedChem 10, 662-687 (2015); U.S. Pat. No. 9,725,467 (B2); EP2914583(B1)). Nitrogen-centered nucleophiles are based on hydrophobic, aliphatic core structure including linear alkanes or branched alkanes, cycloalkanes, methylcycloalkanes.

Scheme B

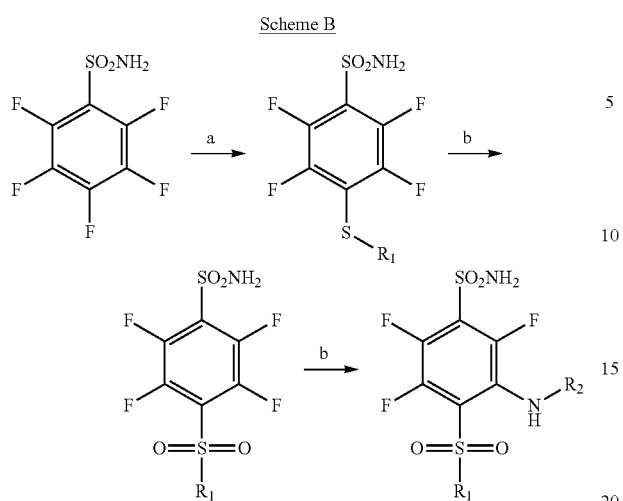

Scheme B. Synthesis of meta and para substituted compounds. Reagents: b) 1) HSR$_1$, Et$_3$N, MeOH; 2) conc. HCl; b) H$_2$O$_2$, CH$_3$COOH, c) 1) NH$_2$R$_2$, Et$_3$N, DMSO; 2) H$_2$O, HCl.

EMBODIMENTS OF THE INVENTION

All starting materials and reagents were commercial products or those which can be prepared according to known procedures. Melting points of the compounds were determined in open capillaries on a Thermo Scientific 9100 Series and are uncorrected. $^1$H and $^{13}$C NMR spectra were recorded on a Bruker spectrometer (400 and 100 MHz, respectively) in DMSO-D$_6$ or CDCl$_3$ using residual DMSO, CDCl$_3$ signals (2.50 ppm, 7.26 ppm and 39.52 ppm, 77.16 ppm for $^1$H and $^{13}$C NMR spectra, respectively) as the internal standard. $^{19}$F NMR spectra were recorded on a Bruker spectrometer (376 MHz) with CFCl$_3$ as an internal standard. TLC was performed with silica gel 60 F$_{254}$ aluminum plates (Merck) and visualized with UV light. Column chromatography was performed using silica gel 60 (0.040-0.063 mm, Merck). High-resolution mass spectra (HRMS) were recorded on a Dual-ESI Q-TOF 6520 mass spectrometer (Agilent Technologies). The purity of final compounds was verified by HPLC. Compound IUPAC names were generated with BIOVIA Draw2021.

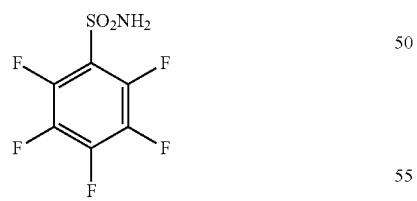

Pentafluorobenzenesulfonamide

Pentafluorobenzenesulfonamide was prepared according to a literature known procedure (Dudutienė, V. et al. *Bioorg. Med. Chem.* 21, 2093-2106 (2013)). The mixture of pentafluorobenzenesulfonyl chloride (1 g, 3.75 mmol) and THF (60 mL) was cooled to ~−10° C. and aqueous ammonia (~1.2 mL, 25%) was added dropwise while stirring. The progress of reaction was monitored by TLC and solution pH was kept at pH~7. THF was evaporated in vacuum and the resultant precipitate was washed with cold H$_2$O. Recrystallization was accomplished from H$_2$O. Yield: 0.84 g (90%), mp 156° C. close to the value in the literature (Dudutienė, V. et al. *Bioorg. Med. Chem.* 21, 2093-2106 (2013)), mp 156-157° C.

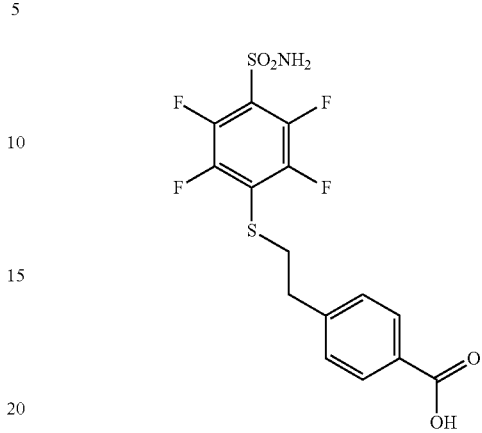

4-[2-(2,3,5,6-Tetrafluoro-4-sulfamoyl-phenyl)sulfanylethyl]benzoic acid

4-[2-(2,3,5,6-Tetrafluoro-4-sulfamoyl-phenyl)sulfanylethyl]benzoic acid was prepared according to a literature known procedure (Kazokaitė, J. et al. *Oncotarget*, 9(42), 26800-26816 (2018)). The mixture of pentafluorobenzenesulfonamide (2.00 g, 8.09 mmol), 4-(2-sulfanylethyl)benzoic acid (1.77 g, 9.71 mmol), Et$_3$N (2.50 mL, 17.9 mmol), and MeOH (20 mL) was stirred at ambient temperature for 24 h. The solution was acidified to pH=5 with conc. HCl and MeOH was removed under reduced pressure. The white solid was washed with water and dried. Recrystallization was accomplished from EtOH. Yield: 2.42 g (73%), mp 235-236° C. close to the value in the literature (Kazokaitė, J. et al. *Oncotarget*, 9(42), 26800-26816 (2018)) mp 235-236° C.

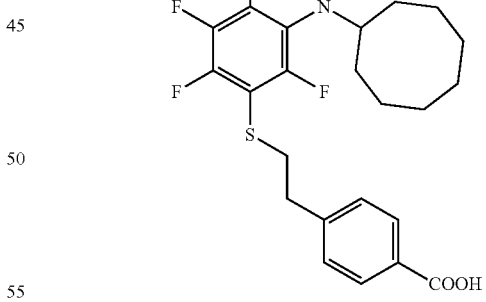

4-[2-[3-(Cyclooctylamino)-2,5,6-trifluoro-4-sulfamoyl-phenyl]sulfanylethyl]benzoic acid (VR16-10)

4-[2-[3-(Cyclooctylamino)-2,5,6-trifluoro-4-sulfamoylphenyl]sulfanylethyl]benzoic acid (VR16-10) was prepared according to a literature known procedure (Kazokaitė, J. et al. *Oncotarget*, 9(42), 26800-26816 (2018)). The mixture of 4-[2-(2,3,5,6-tetrafluoro-4-sulfamoyl-phenyl)sulfanylethyl] benzoic acid (0.40 g, 0.98 mmol), cyclooctylamine (0.214 mL, 1.56 mmol), Et$_3$N (0.34 mL, 2.44 mmol), and DMSO (6 mL) was stirred at 70° C. for 24 h. The solution was cooled to room temperature, diluted with water (20 mL) and acidified to pH=5 with 2 M HCl. The white solid was filtered, washed with water and dried. Recrystallization was accomplished from EtOH:H$_2$O (2:1). Yield: 0.32 g (64%), mp 166-168° C. close to the value in the literature (Kazokaitė, J. et al. *Oncotarget*, 9(42), 26800-26816 (2018)) mp 166-168° C.

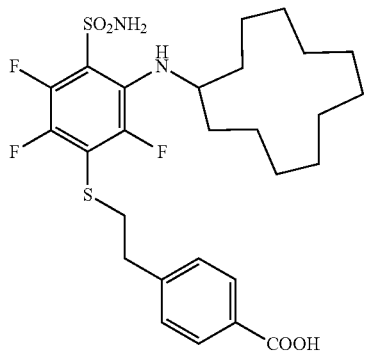 [SMILES: NS(=O)(=O)c1c(F)c(F)c(SCCc2ccc(C(=O)O)cc2)c(F)c1NC1CCCCCCCCCCC1]

4-[2-[3-(Cyclododecylamino)-2,5,6-trifluoro-4-sulfamoyl-phenyl]sulfanylethyl]benzoic acid (VR16-09)

4-[2-[3-(Cyclododecylamino)-2,5,6-trifluoro-4-sulfamoyl-phenyl]sulfanylethyl]benzoic acid (VR16-09) was prepared according to a literature known procedure (Kazokaitė, J. et al. *Oncotarget*, 9(42), 26800-26816 (2018)). The mixture of 4-[2-(2,3,5,6-tetrafluoro-4-sulfamoyl-phenyl)sulfanylethyl]benzoic acid (0.40 g, 0.98 mmol), cyclododecylamine (0.286 g, 1.56 mmol), Et$_3$N (0.34 mL, 2.44 mmol), and DMSO (6 mL) was stirred at 70° C. for 36 h. The solution was cooled to room temperature, diluted with water (20 mL) and acidified to pH=5 with 2 M HCl. The white solid was filtered, washed with water and dried. Recrystallization was accomplished from EtOH:H$_2$O (2:1). Yield: 0.36 g (64%), mp 169-170° C. close to the value in the literature (Kazokaitė, J. et al. *Oncotarget*, 9(42), 26800-26816 (2018)) mp 169-170° C.

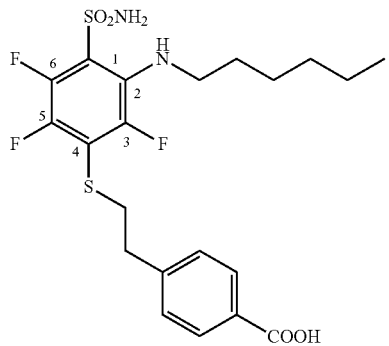 [SMILES: CCCCCCNc1c(F)c(SCCc2ccc(C(=O)O)cc2)c(F)c(F)c1S(N)(=O)=O]

4-[2-[2,3,6-Trifluoro-5-(hexylamino)-4-sulfamoyl-phenyl]sulfanylethyl]benzoic acid (MZ21-06)

The mixture of 4-[2-(2,3,5,6-tetrafluoro-4-sulfamoyl-phenyl)sulfanylethyl]benzoic acid (0.05 g, 0.12 mmol), hexylamine (28.95 uL, 0.2 mmol, 1.7 ekv), Et$_3$N (51 uL, 0.3 mmol, 2.5 ekv) and 3 mL DMSO was heated at 70-75° C. for 20 h. The mixture was diluted with 10 mL of H$_2$O and acidified to pH=3 with diluted HCl. The resulting mixture was extracted with EtOAc (10 mL×3). The extract was dried over Na$_2$SO$_4$ and concentrated under reduced pressure. The resulting brown oil was subjected to column chromatography (silica gel, CHCl$_3$/EtOAc, 3:1, Rf=0.2). Yield: 0.014 g (23%), mp 110-112° C. $^1$H NMR (400 MHz, DMSO-d$_6$, δ): 0.85 (3H, t, J=6.8 Hz, hexane), 1.23-1.35 (6H, m, hexane), 1.46-1.55 (2H, m, hexane), 2.92 (2H, t, J=7.3 Hz, SCH$_2$CH$_2$), 3.22-3.27 (2H, m, hexane), 3.30 (2H, t, J=7.4 Hz, SCH$_2$CH$_2$), 6.27 (1H, br s, NH), 7.34 (2H, t, J=8.2 Hz, ArH), 7.85 (2H, t, J=8.1 Hz, ArH), 8.1 (2H, s, SO$_2$NH$_2$), 12.87 (1H, br. s, COOH). $^{13}$C NMR (100 MHz, DMSO-d$_6$, δ): 14.31 (hexane), 22.46 (hexane), 26.30 (hexane), 30.42 (hexane), 31.39 (hexane), 34.62 (SCH$_2$, t, J=3.2 Hz), 35.89 (SCH$_2$CH$_2$), 46.81 (NHCH$_2$, d, J=11.2 Hz), 117.63 (C4, dd, $^1$J ($^{19}$F-$^{13}$C)=23 Hz, $^2$J ($^{19}$F-$^{13}$C)=19.2 Hz), 118.57 (C1, dd, $^1$J ($^{19}$F-$^{13}$C)=12.4 Hz, $^2$J ($^{19}$F-$^{13}$C)=4.6 Hz), 129.23 (Ar), 129.51 (Ar), 129.81 (Ar), 133.44 (C2, d, $^1$J ($^{19}$F-$^{13}$C)=13 Hz), 141.34 (C5, ddd, $^1$J($^{19}$F-$^{13}$C)=235 Hz, $^2$J ($^{19}$F-$^{13}$C)=15.9 Hz, $^3$J ($^{19}$F-$^{13}$C)=4.6 Hz), 144.69 (C6, ddd, $^1$J ($^{19}$F-$^{13}$C)=249 Hz, $^2$J ($^{19}$F-$^{13}$C)=16 Hz, $^3$J ($^{19}$F-$^{13}$C)=4.1 Hz), 144.93 (Ar), 147.91 (C3, d, $^1$J ($^{19}$F-$^{13}$C)=242.2 Hz), 167.64 (COOH). $^{19}$F NMR (376 MHz, DMSO-d$_6$, δ): −122.07 (1F, d, $^1$J=7.5 Hz), −137.61 (1F, dd, J=27 Hz, $^2$J=11.5 Hz), −145.90 (1F, dd, J=26.8 Hz, $^2$J=3.3 Hz). HRMS for C$_{21}$H$_{25}$F$_3$N$_2$O$_4$S$_2$[(M+H)$^+$]: calc. 491.1281, found 491.1284.

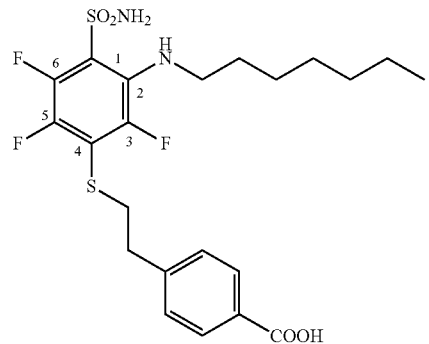 [SMILES: CCCCCCCNc1c(F)c(SCCc2ccc(C(=O)O)cc2)c(F)c(F)c1S(N)(=O)=O]

4-[2-[2,3,6-Trifluoro-5-(heptylamino)-4-sulfamoyl-phenyl]sulfanylethyl]benzoic acid (MZ21-11)

The mixture of 4-[2-(2,3,5,6-tetrafluoro-4-sulfamoyl-phenyl)sulfanylethyl]benzoic acid (0.086 g, 0.21 mmol), heptylamine (50 uL, 0.33 mmol, 1.6 ekv), Et$_3$N (73.53 uL, 0.52 mmol, 2.5 ekv) and 1.5 mL DMSO was heated at 70-75° C. for 16 h. The mixture was diluted with 10 mL of H$_2$O and acidified to pH=4 with diluted HCl. The resulting mixture was extracted with EtOAc (10 mL×3). The extract was dried over Na$_2$SO$_4$ and concentrated under reduced pressure. The resulting transparent oil was subjected to column chromatography (silica gel, EtOAc/CHC$_3$, 1:1, Rf=0.5). Yield: 0.052 g (49%), mp 66-68° C. $^1$H NMR (400 MHz, DMSO-d$_6$, δ): 0.84 (3H, t, J=6.4 Hz, heptane), 1.16-1.36 (8H, m, heptane), 1.44-1.56 (2H, m, heptane), 2.92 (2H, t, J=7.3 Hz, SCH$_2$CH$_2$), 3.24 (2H, br s, heptane), 3.30 (2H, t, J=7.4 Hz, SCH$_2$CH$_2$), 6.26 (1H, s, NH), 7.33 (2H, d, J=8 Hz, ArH), 7.85 (2H, d, J=8 Hz, ArH), 8.09 (2H, s, SO$_2$NH$_2$), 12.83 (1H, br s, COOH). $^{13}$C NMR (100 MHz, DMSO-d$_6$, δ): 14.36 (heptane), 22.46 (heptane), 26.60 (heptane), 28.84 (heptane), 30.46 (d, J($^{19}$F-$^{13}$C)=1.9 Hz, heptane), 31.63 (heptane), 34.62 (t, J($^{19}$F-$^{13}$C)=3.1 Hz, SCH$_2$), 35.90 (SCH$_2$CH$_2$), 46.81 (d, J($^{19}$F-$^{13}$C)=11.2 Hz, NHCH$_2$), 117.63 (C4, dd, $^1$J ($^{19}$F-$^{13}$C)=23.1 Hz, $^2$J ($^{19}$F-$^{13}$C)=18.4 Hz), 118.58 (C1, dd, $^1$J ($^{19}$F-$^{13}$C)=12.2 Hz, $^2$J ($^{19}$F-$^{13}$C)=4.6 Hz), 129.21 (Ar), 129.54 (Ar), 129.81 (Ar), 133.44 (C2, d, J ($^{19}$F-$^{13}$C)=13.9 Hz), 141.34 (C5, ddd, $^1$J ($^{19}$F-$^{13}$C)=236.9 Hz, 2J ($^{19}$F-$^{13}$C)=15.6 Hz, $^3$J ($^{19}$F-$^{13}$C)=4.5 Hz), 144.70 (C6, ddd, $^1$J ($^{19}$F-$^{13}$C)=250.2 Hz, $^2$J ($^{19}$F-$^{13}$C)=15.7 Hz, $^3$J ($^{19}$F-$^{13}$C)=4 Hz), 144.90 (Ar), 147.91 (C3, d, $^1$J ($^{19}$F-$^{13}$C)=241.8 Hz), 167.65 (CO). $^{19}$F NMR (376 MHz, DMSO-d$_6$, δ): −122.06 (1F, d, J=7.7 Hz), −137.60 (1F, dd, J=26.9 Hz, $^2$J=11.5 Hz), −145.90 (1F, dd, J=26.9 Hz, $^2$J=3.8 Hz)). HRMS for C$_{22}$H$_{27}$F$_3$N$_2$4S$_2$ [(M+H)$^+$]: calc. 505.1437, found 505.1454.

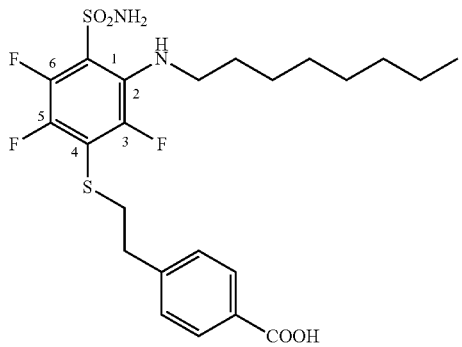 [SMILES: CCCCCCCCNc1c(F)c(SCCc2ccc(C(=O)O)cc2)c(F)c(F)c1S(N)(=O)=O]

4-[2-[2,3,6-Trifluoro-5-(octylamino)-4-sulfamoyl-phenyl]sulfanylethyl]benzoic acid (MZ20-07)

The mixture of 4-[2-(2,3,5,6-tetrafluoro-4-sulfamoyl-phenyl)sulfanylethyl]benzoic acid (0.06 g, 0.147 mmol), octylamine (38.8 uL, 0.235 mmol, 1.6 ekv), Et$_3$N (51 uL, 0.368 mmol, 2.5 ekv) and 3 mL DMSO was heated at 70-75° C. for 12 h. The mixture was diluted with 10 mL of H$_2$O and acidified to pH=4 with diluted HCl. The resulting mixture was extracted with EtOAc (10 mL×3). The extract was dried over Na$_2$SO$_4$ and concentrated under reduced pressure. The resulting brown oil was subjected to column chromatography (silica gel, EtOAc, Rf=0.57). Yield: 0.035 g (46%), mp 69-71° C. $^1$H NMR (400 MHz, DMSO-d$_6$, δ): 0.84 (3H, t, J=6.8 Hz, octane), 1.23-1.34 (10H, m, octane), 1.50 (2H, p, J=7.5 Hz, octane), 2.91 (2H, t, J=7.32 Hz, SCH$_2$CH$_2$), 3.22-3.32 (2H, m, NHCH$_2$), 3.30 (2H, t, J=7.36 Hz, SCH$_2$CH$_2$), 6.27 (1H, br s, NH), 7.37 (2H, d, J=8.13 Hz, ArH), 7.85 (2H, d, J=8.09 Hz, ArH), 8.11 (2H, s, SO$_2$NH$_2$), 12.83 (1H, s, COOH). $^{13}$C NMR (100 MHz, DMSO-d$_6$, δ): 14.39 (octane), 22.53 (octane), 26.62 (octane), 29.06 (octane), 29.13 (octane), 30.43 (d, J=1.9 Hz, octane), 31.65 (octane), 34.61 (SCH$_2$), 35.89 (SCH$_2$CH$_2$), 46.78 (d, J=11.2 Hz, NHCH$_2$), 117.61 (C4, dd, J($^{19}$F-$^{13}$C)=23.18 Hz, $^2$J ($^{19}$F-$^{13}$C)=18.3 Hz), 118.59 (C1, dd, $^1$J ($^{19}$F-$^{13}$C)=12.3 Hz, $^2$J ($^{19}$F-$^{13}$C)=4.9 Hz), 129.23 (Ar), 129.51 (Ar), 129.81 (Ar), 133.43 (C2, d, J ($^{19}$F-$^{13}$C)=14.4 Hz), 141.35 (C5, ddd, $^1$J ($^{19}$F-$^{13}$C)=253.5 Hz, $^2$J ($^{19}$F-$^{13}$C)=15.6 Hz, $^3$J ($^{19}$F-$^{13}$C)=4.3 Hz), 144.71 (C6, ddd, $^1$J ($^{19}$F-$^{13}$C)=251.9 Hz, $^2$J ($^{19}$F-$^{13}$C)=14.9 Hz, $^3$J ($^{19}$F-$^{13}$C)=4.2 Hz), 144.93 (ArC—COOH), 147.93 (C3, dd, $^1$J ($^{19}$F-$^{13}$C)=242.9 Hz, $^2$J ($^{19}$F-$^{13}$C)=2.8 Hz), 167.64 (CO). $^{19}$F NMR (376 MHz, DMSO-d$_6$, δ): −122.07 (1F, d, J=7.56 Hz), −137.61 (1F, dd, $^1$J=20 Hz, $^2$J=11.5 Hz), −145.9 (1F, dd, $^1$J=27 Hz, $^2$J=3.5 Hz). HRMS for C$_{23}$H$_{29}$F$_3$N$_2$O$_4$S$_2$ [(M+H)$^+$]: calc. 519.1594, found 519.1621.

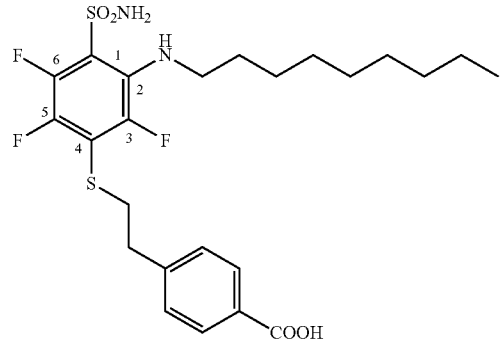 [SMILES: CCCCCCCCCNc1c(F)c(SCCc2ccc(C(=O)O)cc2)c(F)c(F)c1S(N)(=O)=O]

4-[2-[2,3,6-Trifluoro-5-(nonylamino)-4-sulfamoyl-phenyl]sulfanylethyl]benzoic acid (MZ21-12)

The mixture of 4-[2-(2,3,5,6-tetrafluoro-4-sulfamoyl-phenyl)sulfanylethyl]benzoic acid (0.05 g, 0.12 mmol), nonylamine (35.82 uL, 0.19 mmol, 1.6 ekv), Et$_3$N (42.58 uL, 0.3 mmol, 2.5 ekv) and 3 mL DMSO was heated at 70-75° C. for 14 h. The mixture was diluted with 10 mL of H$_2$O and acidified to pH=3 with diluted HCl. The resulting mixture was extracted with EtOAc (10 mL×3). The extract was dried over Na$_2$SO$_4$ and concentrated under reduced pressure. The resulting brown oil was subjected to column chromatography (silica gel, CHCl$_3$/EtOAc, 1:1, Rf=0.25). Yield: 0.023 g (35%), mp 66-67° C. $^1$H NMR (400 MHz, DMSO-d$_6$, δ): 0.84 (3H, t, J=6.6 Hz, nonane), 1.15-1.36 (12H, m, nonane), 1.45-1.55 (2H, m, nonane), 2.92 (2H, t, J=7.4 Hz, SCH$_2$CH$_2$), 3.22-3.27 (2H, m, nonane), 3.3 (2H, t, J=7.5 Hz, SCH$_2$), 6.27 (1H, t, J=4.3 Hz, NH), 7.34 (2H, d, J=8 Hz, ArH), 7.85 (2H, d, J=8 Hz, ArH), 8.09 (SO$_2$NH$_2$), 12.85 (COOH). $^{13}$C NMR (100 MHz, DMSO-d$_6$, δ): 14.39 (nonane), 22.52 (nonane), 26.61 (nonane), 29.07 (nonane), 29.18 (nonane), 29.35 (nonane), 30.43 (nonane, d, J=1.9 Hz), 31.73 (nonane), 34.62 (SCH$_2$, t, J=3.2 Hz), 35.91 (SCH$_2$CH$_2$), 46.68 (NHCH$_2$, d, J=11.3 Hz), 117.6 (C4, dd, $^1$J ($^{19}$F-$^{13}$C)=22.2 Hz, $^2$J ($^{19}$F-$^{13}$C)=19.1 Hz), 118.6 (C1, dd, $^1$J ($^{19}$F-$^{13}$C)=12.3 Hz, $^2$J ($^{19}$F-$^{13}$C)=4.9 Hz), 129.22 (Ar), 129.52 (Ar), 129.81 (Ar), 133.42 (C2, d, $^1$J ($^{19}$F-$^{13}$C)=13.7 Hz), 141.35 (C5, ddd, $^1$J ($^{19}$F-$^{13}$C)=236.8 Hz, $^2$J ($^{19}$F-$^{13}$C)=15.6 Hz, $^3$J ($^{19}$F-$^{13}$C)=3.6 Hz), 144.7 (C6, ddd, $^1$J ($^{19}$F-$^{13}$C)=250.6 Hz, $^2$J ($^{19}$F-$^{13}$C)=16.4 Hz, $^3$J ($^{19}$F-$^{13}$C)=4.1 Hz), 144.91 (Ar), 147.92 (C2, d, $^1$J ($^{19}$F-$^{13}$C)=242.3 Hz), 167.64 (COOH). $^{19}$F NMR (376 MHz, DMSO-d$_6$, δ): −122.05 (1F, d, J=8.5 Hz), −137.60 (1F, dd, $^1$J=27 Hz, $^2$J=11.4 Hz), −145.90 (1F, dd, $^1$J=26.8 Hz, $^2$J=4.1 Hz). HRMS for C$_{24}$H$_{31}$F$_3$N$_2$O$_4$S$_2$ [(M+H)$^+$]: calc. 533.175, found 533.1771.

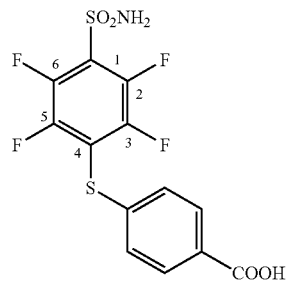 [SMILES: NS(=O)(=O)c1c(F)c(F)c(Sc2ccc(C(=O)O)cc2)c(F)c1F]

4-(2,3,5,6-Tetrafluoro-4-sulfamoyl-phenyl)sulfanyl-benzoic acid (MZ21-01)

The mixture of 2,3,4,5,6-pentafluorobenzenesulfonamide (0.1 g, 0.38 mmol), 4-sulfanylbenzoic acid (0.07 g, 0.45 mmol, 1.2 ekv), Et$_3$N (106 uL, 0.76 mmol, 2 ekv) and 5 mL of MeOH was stirred at room temperature for 4 h. The resulting mixture was acidified to pH=5 with diluted HCl. The precipitate was filtered, washed with water and dried in air. Yield: 0.0951 g (65%), mp 293° C. $^1$H NMR (400 MHz, DMSO-d$_6$, δ): 7.47 (2H, d, J=8.4 Hz, ArH), 7.89 (2H, d, J=8.4 Hz, ArH), 8.51 (2H, s, SO$_2$NH$_2$), 13.11 (COOH). $^{13}$C NMR (100 MHz, DMSO-d$_6$, δ): 115.51 (C1, t, J ($^{19}$F-$^{13}$C)=20.5 Hz), 124.97 (C4, t, J ($^{19}$F-$^{13}$C)=15.5 Hz), 128.48 (Ar), 130.14 (Ar), 130.83 (Ar), 138.42 (Ar), 143.41 (C3 and C5, ddd, $^1$J($^{19}$F-$^{13}$C)=255.6 Hz, $^2$J ($^{19}$F-$^{13}$C)=16.8 Hz, $^3$J ($^{19}$F-$^{13}$C)=5.3 Hz), 147.25 (C2 and C6, ddd, $^1$J ($^{19}$F-$^{13}$C)=246.7 Hz, $^2$J ($^{19}$F-$^{13}$C)=15.8 Hz, $^3$J ($^{19}$F-$^{13}$C)=3.4 Hz), 167.05 (CO). $^{19}$F NMR (376 MHz, DMSO-d$_6$, δ): −131.37: −131.49 (2F, m), −137.88: −138.00 (2F, m). HRMS for C$_{13}$H$_7$F$_4$NO$_4$S$_2$[(M−H)$^-$]: calc. 379.9680, found 379.9695.

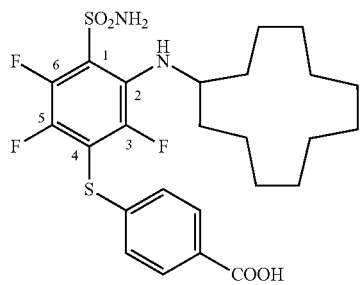 [SMILES: NS(=O)(=O)c1c(F)c(F)c(Sc2ccc(C(=O)O)cc2)c(F)c1NC1CCCCCCCCCCC1]

4-[3-(Cyclododecylamino)-2,5,6-trifluoro-4-sulfamoyl-phenyl]sulfanylbenzoic acid (MZ21-02)

The mixture of 4-(2,3,5,6-tetrafluoro-4-sulfamoyl-phenyl)sulfanylbenzoic acid (MZ21-01) (0.081 g, 0.14 mmol), cyclododecylamine (0.061 g, 0.33 mmol, 1.6 ekv), Et$_3$N (73 uL, 0.52 mmol, 2.5 ekv) and 3 mL of DMSO was heated at 70-75° C. for 18 h. The mixture was diluted with 10 mL of H$_2$O and acidified to pH=5 with diluted HCl. The brown precipitate was filtered and recrystallized from acetone:water (1:1). Yield: 0.038 g (34%), mp 186-188° C. $^1$H NMR (400 MHz, DMSO-d$_6$, δ): 1.10-1.73 (22H, m, cyclododecane), 3.57 (1H, br s, CH of cyclododecane), 6.25 (1H, d, J=8.1 Hz, NH), 7.42 (2H, d, J=8.3 Hz, ArH), 7.93 (2H, d, J=8.3 Hz, ArH), 8.29 (3H, br s, SO$_2$NH$_2$, COOH). $^{13}$C NMR (100 MHz, DMSO-d$_6$, δ): 21.31 (cyclododecane), 23.21 (cyclododecane), 23.43 (cyclododecane), 23.86 (cyclododecane), 28.24 (cyclododecane), 31.05 (cyclododecane), 52.66 (CH of cyclododecane, d, J=10.6 Hz), 115.38 (C4, dd, $^1$J ($^{19}$F-$^{13}$C)=23.1 Hz, $^2$J ($^{19}$F-$^{13}$C)=18.8 Hz), 121.32 (C1, dd, $^1$J ($^{19}$F-$^{13}$C)=11.9 Hz, $^2$J ($^{19}$F-$^{13}$C)=4.5 Hz), 128.18 (Ar), 128.63 (Ar), 130.72 (Ar), 133.38 (C2, d, 1J ($^{19}$F-$^{13}$C)=14.8 Hz), 137.68 (Ar), 141.59 (C5, ddd, $^1$J ($^{19}$F-$^{13}$C)=239.5 Hz, $^2$J ($^{19}$F-$^{13}$C)=16.6, $^3$J ($^{19}$F-$^{13}$C)=3.9 Hz), 145.02 (C6, ddd, $^1$J ($^{19}$F-$^{13}$C)=251.9 Hz, $^2$J ($^{19}$F-$^{13}$C)=14.8 Hz, $^3$J ($^{19}$F-$^{13}$C)=3.4 Hz), 148.42 (C3, d, $^1$J ($^{19}$F-$^{13}$C)=246.2 Hz), 167.64 (COOH). $^{19}$F NMR (376 MHz, DMSO-d$_6$, δ): −118.57 (1F, d, J=9.6 Hz), −136.01 (1F, dd, $^1$J=27.1 Hz, $^2$J=11.9 Hz), −144.26 (1F, dd, J=27 Hz, $^2$J=4.3 Hz). HRMS for C$_{25}$H$_{31}$F$_3$N$_2$O$_4$S$_2$ [(M+H)$^+$]: calc. 545.175, found 545.1754.

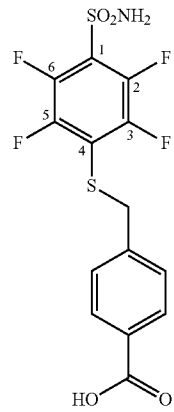

4-[(2,3,5,6-Tetrafluoro-4-sulfamoyl-phenyl)sulfanylmethyl]benzoic acid (MZ21-09)

The mixture of 2,3,4,5,6-pentafluorobenzenesulfonamide (0.1 g, 0.41 mmol), 4-(sulfanylmethyl)benzoic acid (0.083 g, 0.49 mmol, 1.2 ekv), Et$_3$N (115 uL, 0.82 mmol, 2 ekv) and 5 mL of MeOH was stirred at room temperature for 3 h. The resulting mixture was acidified to pH=5 with diluted HCl. The precipitate was filtered, washed with water and dried in air. Yield: 0.127 g (78%), decomposes at 266° C. $^1$H NMR (400 MHz, DMSO-d$_6$, δ): 4.35 (2H, s, SCH$_2$), 7.38 (2H, t, J=8.2 Hz, ArH), 7.86 (2H, t, J=8.2 Hz, ArH), 8.42 (2H, s, SO$_2$NH$_2$), 12.94 (1H, br s, COOH). $^{13}$C NMR (100 MHz, DMSO-d$_6$, δ): 37.98 (SCH$_2$), 117.86 (C1, t, J($^{19}$F-$^{13}$C)=20.9 Hz), 123.62 (C4, t, J($^{19}$F-$^{13}$C)J=15.4 Hz), 129.39 (Ar), 130 (Ar), 130.43 (Ar), 142.48 (Ar), 142.86 (C2 and C6, dd, $^1$J ($^{19}$F-$^{13}$C)=255.7 Hz, $^2$J ($^{19}$F-$^{13}$C)=16.9 Hz), 147.09 (C3 and C5, dd, $^1$J ($^{19}$F-$^{13}$C)=247.66 Hz, $^2$J ($^{19}$F-$^{13}$C)=13.50 Hz), 167 (COOH). $^{19}$F NMR (376 MHz, DMSO-d$_6$, δ): −132.09: −132.24 (2F, m), −138.90: −139.05 (2F, m). HRMS for C$_{14}$H$_9$F$_4$NO$_4$S$_2$[(M−H)$^-$]: calc. 393.9836, found 393.9840.

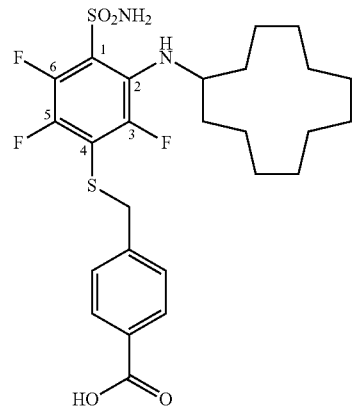 [SMILES: NS(=O)(=O)c1c(F)c(F)c(SCc2ccc(C(=O)O)cc2)c(F)c1NC1CCCCCCCCCCC1]

4-[[3-(Cyclododecylamino)-2,5,6-trifluoro-4-sulfamoyl-phenyl]sulfanylmethyl]benzoic acid (MZ21-10)

The mixture of 4-[(2,3,5,6-tetrafluoro-4-sulfamoyl-phenyl)sulfanylmethyl]benzoic acid (MZ21-09) (0.127 g, 0.32 mmol), cyclododecylamine (0.105 g, 0.57 mmol, 1.8 ekv), Et$_3$N (119 uL, 0.86 mmol, 2.7 ekv) and 2 mL DMSO was heated at 70-75° C. for 21 h. The mixture was diluted with 10 mL of H$_2$O and acidified to pH=4 with diluted HCl. The resulting mixture was extracted with EtOAc (10 mL×3). The extract was dried over Na$_2$SO$_4$ and concentrated under reduced pressure. The resulting brown oil was subjected to column chromatography (silica gel, EtOAc/CHCl$_3$, 1:1, Rf=0.25). Yield: 0.028 g (15%), mp 190-191° C. $^1$H NMR (400 MHz, DMSO-d$_6$, δ): 1.13-1.54 (22H, m, cyclododecane), 3.55 (1H, br s, CH of cyclododecane), 4.27 (2H, s, SCH$_2$), 6.16 (1H, d, J=8.7 Hz, NH), 7.34 (2H, t, J=8.1 Hz, ArH), 7.84 (2H, t, J=8.1 Hz, ArH), 8.12 (1H, s, SO$_2$NH$_2$), 12.94 (1H, br s, COOH). $^{13}$C NMR (100 MHz, DMSO-d$_6$, δ): 21.01 (cyclododecane), 23.13 (cyclododecane), 23.27 (cyclododecane), 24.10 (cyclododecane), 24.30 (cyclododecane), 30.51 (cyclododecane), 37.80 (SCH$_2$), 52.87 (CH of cyclododecane, d, J=10.8 Hz), 116.51 (C4, dd, $^1$J($^{19}$F-$^{13}$C) =23.9 Hz, $^2$J ($^{19}$F-$^{13}$C)=19 Hz), 119.85 (C1, dd, $^1$J ($^{19}$F-$^{13}$C) =12 Hz, $^2$J ($^{19}$F-$^{13}$C)=4.7 Hz), 129.14 (Ar), 129.89 (Ar), 130.30 (Ar), 132.67 (C2, d, $^1$J ($^{19}$F-$^{13}$C)=15.4 Hz), 141.69 (C5, ddd, $^1$J ($^{19}$F-$^{13}$C)=236 Hz, $^2$J ($^{19}$F-$^{13}$C)=15.4 Hz, $^3$J ($^{19}$F-$^{13}$C)=4.2 Hz), 142.81 (Ar), 144.66 (C6, ddd, $^1$J ($^{19}$F-$^{13}$C)=250.7 Hz, $^2$J ($^{19}$F-$^{13}$C)=16.1 Hz, $^3$J ($^{19}$F-$^{13}$C)=4.2 Hz), 148.49 (C3, d, $^1$J ($^{19}$F-$^{13}$C)=243.5 Hz), 167.37 (COOH). $^{19}$F NMR (376 MHz, DMSO-d$_6$, δ): −120.13 (1F, d, $^1$J=11.28 Hz), −137.13 (1F, dd, J=27.2 Hz, $^2$J=11.7 Hz), −144.74 (1F, dd, J=27.2 Hz, $^2$J=3.1 Hz). HRMS for C$_{26}$H$_{33}$F$_3$N$_2$O$_4$S$_2$ [(M+H)$^+$]: calc. 559.1907, found 551.1490.

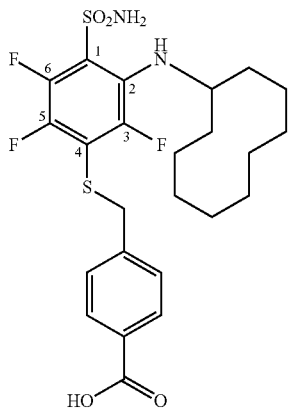 [SMILES: NS(=O)(=O)c1c(F)c(F)c(SCc2ccc(C(=O)O)cc2)c(F)c1NC1CCCCCCCCC1]

4-[[3-(Cyclodecylamino)-2,5,6-trifluoro-4-sulfamoyl-phenyl]sulfanylmethyl]benzoic acid (MZ21-25)

The mixture of 4-[(2,3,5,6-tetrafluoro-4-sulfamoyl-phenyl)sulfanylmethyl]benzoic acid (MZ21-09) (0.083 g, 0.21 mmol), cyclodecanamine hydrochloride (0.0485 g, 0.252 mmol, 1.2 ekv), Et$_3$N (94 uL, 0.672 mmol, 3.2 ekv) and 3 mL DMSO was heated at 60° C. for 5 days. Then another 1.2 ekv of cyclodecanamine hydrochloride and 3.2 ekv Et$_3$N were added, the heating was continued for another 5 days. The mixture was diluted with 10 mL of H$_2$O and acidified to pH=2 with diluted HCl. The resulting mixture was extracted with EtOAc (10 mL×3). The extract was dried over MgSO$_4$ and concentrated under reduced pressure. The resulting dark yellow oil was subjected to column chromatography (silica gel, CHCl$_3$/MeOH, 8:1, Rf=0.166). Yield: 0.01 g (9%), mp 176° C. $^1$H NMR (400 MHz, DMSO-d$_6$, δ): 1.16-1.66 (18H, m, cyclodecane), 3.68 (1H, br s, NHCH), 4.27 (2H, s, SCH$_2$), 6.15 (1H, d, J=8.9 Hz, NH), 7.33 (2H, d, J=8.1 Hz, ArH), 7.83 (2H, d, J=8 Hz, ArH), 8.11 (2H, s, SO$_2$NH$_2$), 12.93 (1H, br s, COOH). $^{13}$C NMR (100 MHz, DMSO-d$_6$, δ): 22.28 (cyclodecane), 24.25 (cyclodecane), 25.22 (cyclodecane), 25.25 (cyclodecane) 31.12 (cyclodecane), 37.78 (SCH$_2$), 38.56 (cyclodecane), 54.55 (NHCH, d, $^1$J ($^{19}$F-$^{13}$C)=10.5 Hz), 116.35 (C4, dd, $^1$J ($^{19}$F-$^{13}$C)=23.9 Hz, $^2$J ($^{19}$F-$^{13}$C)=19.6 Hz), 120.08 (C1, dd, $^1$J ($^{19}$F-$^{13}$C)= 11.9 Hz, $^2$J ($^{19}$F-$^{13}$C)=4.7 Hz), 129.19 (Ar), 129.87 (Ar), 130.32 (Ar), 132.49 (C2, d, J ($^{19}$F-$^{13}$C)=15.8 Hz), 141.85 (C5, ddd, $^1$J ($^{19}$F-$^{13}$C)=237 Hz, 2J ($^{19}$F-$^{13}$C)=14.5 Hz, 3J ($^{19}$F-$^{13}$C)=4.4 Hz), 142.80 (Ar), 144.60 (C6, ddd, $^1$J ($^{19}$F-$^{13}$C)=250.2 Hz, $^2$J ($^{19}$F-$^{13}$C)=15.7 Hz, $^3$J ($^{19}$F-$^{13}$C)=4 Hz), 148.29 (C3, d, J ($^{19}$F-$^{13}$C)=243.5 Hz), 167.40 (CO). $^{19}$F NMR (376 MHz, DMSO-d$_6$, δ): −119.85 (1F, d, J=11 Hz), −137.19 (1F, dd, $^1$J=27.2 Hz, $^2$J=11.8 Hz), −144.48 (1F, dd, $^1$J=27.2 Hz, $^2$J=3 Hz). HRMS for C$_{24}$H$_{29}$F$_3$N$_2$O$_4$S$_2$ [(M+H)$^+$]: calc. 531.1594, found 531.1593.

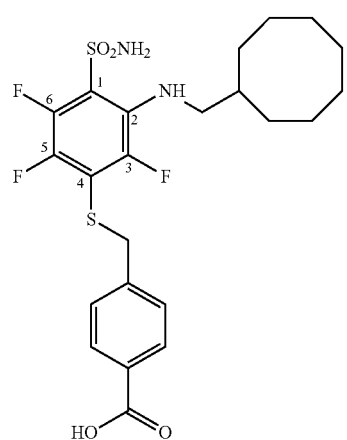 [SMILES: NS(=O)(=O)c1c(F)c(F)c(SCc2ccc(C(=O)O)cc2)c(F)c1NCC1CCCCCCC1]

4-[[3-(Cyclooctylmethylamino)-2,5,6-trifluoro-4-sulfamoyl-phenyl]sulfanylmethyl]benzoic acid (MZ21-23)

The mixture of 4-[(2,3,5,6-tetrafluoro-4-sulfamoyl-phenyl)sulfanylmethyl]benzoic acid (MZ21-09) (0.065 g, 0.166 mmol), cyclooctylmethanamine (43.7 uL, 0.26 mmol, 1.6 ekv), Et$_3$N (57.84 uL, 0.415 mmol, 2.5 ekv) and 2.5 mL DMSO was heated at 85° C. for 14 h. The mixture was diluted with 10 mL of H$_2$O and acidified to pH=3 with diluted HCl. The resulting mixture was extracted with EtOAc (10 mL×3). The extract was dried over Na$_2$SO$_4$ and concentrated under reduced pressure. The resulting brown residue was subjected to column chromatography (silica gel, EtOAc/CHCl$_3$, 1:1, Rf=0.15). Yield: 0.018 g (22%), mp 157-158° C. $^1$H NMR (400 MHz, DMSO-d$_6$, δ): 1.15-1.68 (15H, m, cyclooctane), 2.88-3.01 (2H, m, NHCH$_2$), 4.26 (2H, s, SCH$_2$), 6.30 (1H, br s, NH), 7.35 (2H, d, J=7.8 Hz, ArH), 7.85 (2H, d, J=7.7 Hz, ArH), 8.10 (2H, br s, SO$_2$NH$_2$), 12.92 (1H, br s, COOH). $^{13}$C NMR (100 MHz, DMSO-d$_6$, δ): 25.29 (cyclooctane), 26.27 (cyclooctane), 27.00 (cyclooctane), 30.01 (cyclooctane), 37.87 (SCH$_2$), 38.50 (CH of cyclooctane, d, J($^{19}$F-$^{13}$C)=2 Hz), 53.71 (NHCH$_2$, d, J($^{19}$F-$^{13}$C)=10.7 Hz), 116.63 (C4, dd, $^1$J ($^{19}$F-$^{13}$C)=24 Hz, $^2$J ($^{19}$F-$^{13}$C)=19.4 Hz), 118.96 (C1, dd, $^1$J ($^{19}$F-$^{13}$C)=11 Hz, $^2$J ($^{19}$F-$^{13}$C)=4.6 Hz), 129.30 (Ar), 129.89 (Ar), 130.33 (Ar), 133.59 (C2, d, J ($^{19}$F-$^{13}$C)=13.4 Hz), 141.64 (C5, ddd, $^1$J ($^{19}$F-$^{13}$C)=236 Hz, $^2$J ($^{19}$F-$^{13}$C)=15.6 Hz, $^3$J ($^{19}$F-$^{13}$C)=4.3

Hz), 142.77 (Ar), 144.68 (C6, ddd, $^1J$ ($^{19}F$-$^{13}C$)=250 Hz, $^2J$ ($^{19}F$-$^{13}C$)=15.8 Hz, $^3J$ ($^{19}F$-$^{13}C$)=3.8 Hz), 148.22 (C3, d, J ($^{19}F$-$^{13}C$)=243.3 Hz) 167.41 (CO). $^{19}F$ NMR (376 MHz, DMSO-$d_6$, δ): −120.67 (1F, d, J=8.1 Hz), −137.58 (1F, dd, J=27.2 Hz, $^2J$=11.7 Hz), −145.51 (1F, dd, J=27.2 Hz, $^2J$=4.1 Hz). HRMS for $C_{23}H_{27}F_3N_2O_4S_2$ [(M+H)$^+$]: calc. 517.1437, found 517.1463.

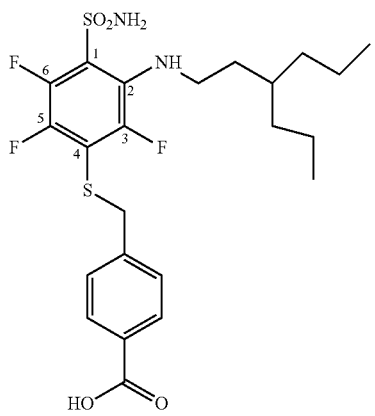 [SMILES: CCCC(CCC)CCNc1c(F)c(SCc2ccc(C(=O)O)cc2)c(F)c(F)c1S(N)(=O)=O]

4-[[2,3,6-Trifluoro-5-(3-propylhexylamino)-4-sulfamoyl-phenyl]sulfanylmethyl]benzoic acid (MZ21-35)

The mixture of 4-[(2,3,5,6-tetrafluoro-4-sulfamoyl-phenyl)sulfanylmethyl]benzoic acid (MZ21-09) (0.077 g, 0.195 mmol), 3-propylhexan-1-amine hydrochloride (0.042 g, 0.23 mmol, 1.6 ekv), $K_2CO_3$ (0.094 g, 0.68 mmol, 3.5 ekv) and 3 mL DMSO was heated at 60° C. for 3 days. The mixture was diluted with 10 mL of $H_2O$ and acidified to pH=3 with diluted HCl. The resulting mixture was extracted with EtOAc (10 mL×3). The extract was dried over $MgSO_4$ and concentrated under reduced pressure. The resulting brown residue was subjected to column chromatography silica gel, EtOAc/CHCl$_3$, 1:1, Rf=0.23). Yield: 0.059 g (59%), mp 149° C. $^1H$ NMR (400 MHz, DMSO-$d_6$, δ): 0.85-1.40 (17H, m, 3-propylheptane), 3.16 (2H, s, NHCH$_2$), 4.28 (2H, s, SCH$_2$), 6.16 (1H, br s, NH), 7.36 (2H, d, J=7.3 Hz, ArH), 7.85 (2H, d, J=7.3 Hz, ArH), 8.1 (2H, s, SO$_2$NH$_2$), 12.93 (1H, s, COOH). $^{13}C$ NMR (100 MHz, DMSO-$d_6$, δ): 14.75 (3-propylheptane), 19.57 (3-propylheptane), 34.34 (4-propylheptane), 34.47 (4-propylheptane), 35.83 (4-propylheptane), 37.79 (SCH$_2$), 44.69 (d, J ($^{19}F$-$^{13}C$)=11.2 Hz, NHCH$_2$), 116.66 (C4, dd, $^1J$ ($^{19}F$-$^{13}C$)=23.1 Hz, $^2J$ ($^{19}F$-$^{13}C$)=19.3 Hz), 119.26 (C1, dd, $^1J$ ($^{19}F$-$^{13}C$)=11.8 Hz, $^2J$ ($^{19}F$-$^{13}C$)=4.7 Hz), 129.28 (Ar), 129.90 (Ar), 130.30 (Ar), 133.36 (C2, d, J ($^{19}F$-$^{13}C$)=11.9 Hz), 141.53 (C5, ddd, $^1J$ ($^{19}F$-$^{13}C$)=238.2 Hz, $^2J$ ($^{19}F$-$^{13}C$)=15.5 Hz, $^3J$ ($^{19}F$-$^{13}C$)=4.4 Hz), 142.79 (Ar), 144.50 (C6, ddd, $^1J$ ($^{19}F$-$^{13}C$)=252.5 Hz, $^2J$ ($^{19}F$-$^{13}C$)=16.8 Hz, $^3J$ ($^{19}F$-$^{13}C$)=4.4 Hz), 148.33 (C3, d, $^1J$ ($^{19}F$-$^{13}C$)=242.7 Hz), 167.39 (CO). $^{19}F$ NMR (376 MHz, DMSO-$d_6$, δ): −121.07 (1F, s), −137.62 (1F, dd, J=27 Hz, $^2J$=11.5 Hz), −145.19 (1F, d, J=26.3 Hz). HRMS for $C_{23}H_{29}F_3N_2O_4S_2$ [(M+H)$^+$]: calc. 519.1594, found 519.1593.

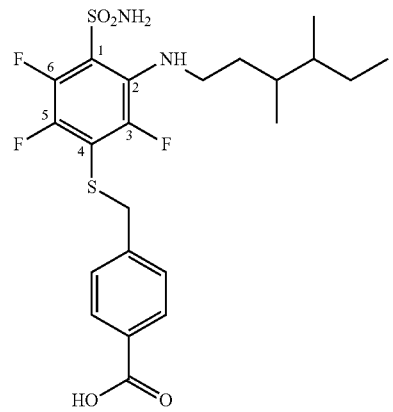 [SMILES: CCC(C)C(C)CCNc1c(F)c(SCc2ccc(C(=O)O)cc2)c(F)c(F)c1S(N)(=O)=O]

4-[[3-(3,4-Dimethylhexylamino)-2,5,6-trifluoro-4-sulfamoyl-phenyl]sulfanylmethyl]benzoic acid (MZ21-40)

The mixture of 4-[(2,3,5,6-tetrafluoro-4-sulfamoyl-phenyl)sulfanylmethyl]benzoic acid (MZ21-09) (0.06 g, 0.151 mmol) (MZ21-09), 3,4-dimethylhexan-1-amine (0.04 g, 0.242 mmol, 1.6 ekv), Et$_3$N (76 uL, 0.54 mmol, 3.6 ekv) and 5 mL DMSO was heated at 60° C. for 3 days. The mixture was diluted with 10 mL of $H_2O$ and acidified to pH=2 with diluted HCl. The resulting mixture was extracted with EtOAc (10 mL×3). The extract was dried over $MgSO_4$ and concentrated under reduced pressure. The resulting dark yellow oil was subjected to column chromatography (silica gel, Hex/PrOH, 4:1, Rf=0.28). Yield: 0.011 g (14%), mp 133° C. $^1H$ NMR (400 MHz, DMSO-$d_6$, δ): 0.69-1.57 (15H, m, 3,4-dimethylhexane), 3.18 (2H, br d, J=24.8 Hz, NHCH$_2$), 4.27 (2H, s, SCH$_2$), 6.18 (1H, br s, NH), 7.34 (2H, d, J=8.1 Hz, ArH), 7.84 (2H, d, J=8.1 Hz, ArH), 8.11 (2H, br s, SO$_2$NH$_2$), unresolved (1H, br s, COOH). $^{13}C$ NMR (100 MHz, DMSO-$d_6$, δ): 12.44 (3,4-dimethylhexane), 14.41 (3,4-dimethylhexane), 14.47 (3,4-dimethylhexane), 16.06 (3,4-dimethylhexane), 16.80 (3,4-dimethylhexane), 25.59 (3,4-dimethylhexane), 27.22 (3,4-dimethylhexane), 33.39 (3,4-dimethylhexane), 33.53 (3,4-dimethylhexane), 34.42 (3,4-dimethylhexane), 35.44 (3,4-dimethylhexane), 37.81 (3,4-dimethylhexane), 38.42 (3,4-dimethylhexane), 39.29 (3,4-dimethylhexane), 45.23 (NHCH, dd, $^1J$ ($^{19}F$-$^{13}C$)= 11 Hz, $^2J$ ($^{19}F$-$^{13}C$)=6.7 Hz), 116.72 (C4, dd, $^1J$($^{19}F$-$^{13}C$)=23 Hz, $^2J$ ($^{19}F$-$^{13}C$)=19.1 Hz), 119.14 (C1, dd, $^1J$ ($^{19}F$-$^{13}C$)=12 Hz, $^2J$ ($^{19}F$-$^{13}C$)=5 Hz), 129.15 (Ar), 129.87 (Ar), 133.38 (C2, d, J ($^{19}F$-$^{13}C$)=14.2 Hz), 141.49 (C5, ddd, $^1J$ ($^{19}F$-$^{13}C$)=233 Hz, $^2J$ ($^{19}F$-$^{13}C$)=14 Hz, $^3J$ ($^{19}F$-$^{13}C$)=4 Hz), 142.25 (Ar), 144.50 (C6, ddd, $^1J$ ($^{19}F$-$^{13}C$)=249 Hz, $^2J$ ($^{19}F$-$^{13}C$)=15 Hz, $^3J$ ($^{19}F$-$^{13}C$)=3.3 Hz), 148.29 (C3, d, $^1J$($^{19}F$-$^{13}C$)=242.7 Hz), 167.84 (CO). $^{19}F$ NMR (376 MHz, DMSO-$d_6$, δ): −121.15 (1F, dd, J=46.5 Hz, $^2J$=8.5 Hz), −137.63 (1F, dd, J=27.2 Hz, $^2J$=9.8 Hz), −145.23 (1F, td, J=26.8 Hz, $^2J$=3.9 Hz). HRMS for $C_{22}H_{27}F_3N_2O_4S_2$ [(M+H)$^+$]: calc. 505.1437, found 505.1440.

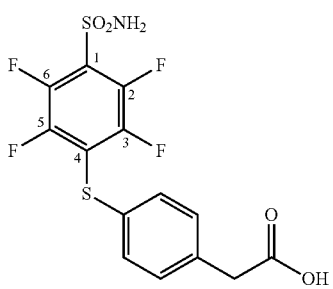 [SMILES: NS(=O)(=O)c1c(F)c(F)c(Sc2ccc(CC(=O)O)cc2)c(F)c1F]

2-[4-(2,3,5,6-Tetrafluoro-4-sulfamoyl-phenyl)sulfanylphenyl]acetic acid (MZ21-17)

The mixture of 2,3,4,5,6-pentafluorobenzenesulfonamide (0.05 g, 0.2 mmol), 2-(4-sulfanylphenyl)acetic acid (0.04 g, 0.24 mmol, 1.2 ekv), Et$_3$N (56 uL, 0.4 mmol, 2 ekv) and 5 mL of MeOH was stirred at room temperature for 4 h. The resulting mixture was acidified to pH=5 with diluted HCl. The precipitate was filtered, washed with water and dried in air. Yield: 0.056 g (72%), mp 236-238° C. $^1$H NMR (400 MHz, DMSO-d$_6$, δ): 3.58 (2H, s, CH$_2$COOH), 7.27 (2H, d, J=6.6 Hz, ArH), 7.38 (2H, d, J=6.9 Hz, ArH), 8.44 (2H, s, SO$_2$NH$_2$), 12.41 (1H, br s, COOH). $^{13}$C NMR (100 MHz, DMSO-d$_6$, δ): 46.10 (CH$_2$), 117.69 (C1, t, J ($^{19}$F-$^{13}$C)=20.1 Hz), 124.16 (C4, t, J($^{19}$F-$^{13}$C)=15.7 Hz), 130.12 (Ar), 130.33 (Ar), 131.27 (Ar), 135.80 (Ar), 143.27 (C3 and C5, dd, $^1$J ($^{19}$F-$^{13}$C)=256 Hz, $^2$J ($^{19}$F-$^{13}$C)=16 Hz), 146.89 (C2 and C6, dd, $^1$J ($^{19}$F-$^{13}$C)=245.8 Hz, $^2$J ($^{19}$F-$^{13}$C)=17.3 Hz), 172.77 (CO). $^{19}$F NMR (376 MHz, DMSO-d$_6$, δ): −131.90: −132.60 (2F, m), −138.12: −138.72 (2F, m). HRMS for C$_{14}$H$_9$F$_4$NO$_4$S$_2$[(M−H)$^-$]: calc. 393.9836, found 393.9845.

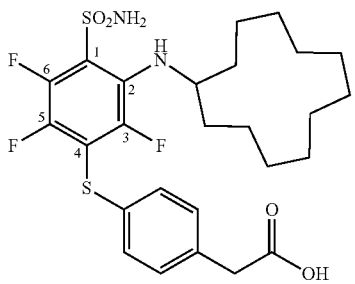 [SMILES: NS(=O)(=O)c1c(F)c(F)c(Sc2ccc(CC(=O)O)cc2)c(F)c1NC1CCCCCCCCCCC1]

2-[4-(3-(Cyclododecylamino)-2,5,6-trifluoro-4-sulfamoylphenyl)sulfanylphenyl]acetic acid (MZ21-18)

The mixture of 2-(4-(2,3,5,6-tetrafluoro-4-sulfamoylphenyl)sulfanylphenyl)acetic acid (MZ21-17) (0.08 g, 0.2 mmol), cyclododecylamine (0.059, 0.32 mmol, 1.6 ekv), Et$_3$N (70 uL, 0.5 mmol, 2.5 ekv) and 2 mL DMSO was stirred at 80° C. for 21 h. The mixture was diluted with 10 mL of H$_2$O and acidified to pH=4 with diluted HCl. The resulting mixture was extracted with EtOAc (10 mL×3). The extract was dried over Na$_2$SO$_4$ and concentrated under reduced pressure. The resulting brown residue was subjected to column chromatography (silica gel, EtOAc, Rf=0.57). Yield: 0.042 g (37%), mp 148-150° C. $^1$H NMR (400 MHz, DMSO-d$_6$, δ): 1.15-1.60 (22H, m, cyclododecane), 3.56 (2H, s, CH$_2$COOH), 3.62 (1H, br s, CH of cyclododecane), 6.22 (1H, d, J=8.9 Hz, NH), 7.25 (2H, d, J=8.3 Hz, ArH), 7.29 (2H, d, J=8.2 Hz, ArH), 8.16 (SO$_2$NH$_2$), 12.37 (COOH). $^{13}$C NMR (100 MHz, DMSO-d$_6$, δ): 21.19 (cyclododecane), 23.20 (cyclododecane), 23.38 (cyclododecane), 23.76 (cyclododecane), 24.07 (cyclododecane), 30.83 (cyclododecane), 42.60 (CH$_2$COOH), 52.73 (CH of cyclododecane, d, J($^{19}$F-$^{13}$C)=10 Hz), 116.64 (C4, dd, $^1$J ($^{19}$F-$^{13}$C)=23.4 Hz, $^2$J ($^{19}$F-$^{13}$C)=18.8 Hz), 120.72 (C1, dd, $^1$J ($^{19}$F-$^{13}$C)=12.3 Hz, $^2$J ($^{19}$F-$^{13}$C)=4.5 Hz), 129.69 (Ar), 131.12 (Ar), 131.23 (Ar), 133.21 (C2, d, J ($^{19}$F-$^{13}$C)=11.7 Hz), 135.23 (Ar), 141.47 (C5, ddd, $^1$J ($^{19}$F-$^{13}$C)=239.4 Hz, $^2$J ($^{19}$F-$^{13}$C)=15.5 Hz, $^3$J ($^{19}$F-$^{13}$C)=3 Hz), 144.97 (C6, ddd, $^1$J ($^{19}$F-$^{13}$C)=250.9 Hz, $^2$J ($^{19}$F-$^{13}$C)=15.8 Hz, $^3$J ($^{19}$F-$^{13}$C)= 4.3 Hz), 148.30 (C3, d, $^1$J ($^{19}$F-$^{13}$C)=245.6 Hz), 172.73 (CO). $^{19}$F NMR (376 MHz, DMSO-d$_6$, δ): −119.40 (1F, d, J=10.8 Hz), −136.28 (1F, dd, $^1$J=27.1 Hz, $^2$J=11.7 Hz), −144.52 (1F, dd, $^1$J=27.2 Hz, $^2$J=4.1 Hz). HRMS for C$_{26}$H$_{33}$F$_3$N$_2$O$_4$S$_2$ [(M+H)$^+$]: calc. 559.1907, found 559.1904.

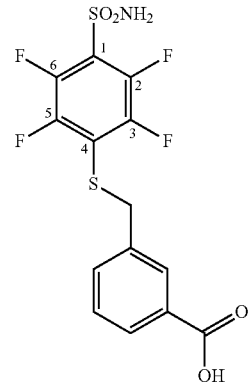 [SMILES: NS(=O)(=O)c1c(F)c(F)c(SCc2cccc(C(=O)O)c2)c(F)c1F]

3-[(2,3,5,6-Tetrafluoro-4-sulfamoylphenyl)sulfanylmethyl]benzoic acid (MZ21-24)

The mixture of 2,3,4,5,6-pentafluorobenzenesulfonamide (0.05 g, 0.2 mmol), 3-(sulfanylmethyl)benzoic acid (0.04 g, 0.24 mmol, 1.2 ekv), Et$_3$N (56 uL, 0.4 mmol, 2 ekv) and 5 mL of MeOH was stirred at room temperature for 4 h. The resulting mixture was acidified to pH=5 with diluted HCl. The precipitate was filtered, washed with water and dried in air. Yield: 0.061 g (77%), mp 229° C. $^1$H NMR (400 MHz, DMSO-d$_6$, δ): 4.36 (2H, s, SCH$_2$), 7.35-7.55 (2H, m, ArH), 7.75-7.95 (2H, m, ArH), 7.42 (1H, t, J=7.4 Hz, ArH), 7.49 (1H, d, J=7.4 Hz, ArH), 7.83 (1H, d, J=7.4 Hz, ArH), 7.90 (1H, s, ArH), 8.40 (2H, s, SO$_2$NH$_2$), 13.00 (1H, br s, COOH). $^{13}$C NMR (100 MHz, DMSO-d$_6$, δ): 37.97 (SCH$_2$), 118.04 (C1, t, $^1$J ($^{19}$F-$^{13}$C)=20.9 Hz), 123.57 (C4, t, J ($^{19}$F-$^{13}$C)=15.7 Hz), 128.99 (Ar), 129.98 (Ar), 130.13 (Ar), 131.57 (Ar), 133.53 (Ar), 137.93 (Ar), 142.88 (C3 and C5, ddt, $^1$J($^{19}$F-$^{13}$C)=255 Hz, $^2$J ($^{19}$F-$^{13}$C)=17.2 Hz, $^3$J ($^{19}$F-$^{13}$C)= 4.3 Hz), 146.89 (C2 and C6, ddt, $^1$J ($^{19}$F-$^{13}$C)=246.4 Hz, 2J ($^{19}$F-$^{13}$C)=15.2 Hz, $^3$J ($^{19}$F-$^{13}$C)=3.3 Hz), 167.37 (CO). $^{19}$F NMR (376 MHz, DMSO-d$_6$, δ): −132.11: −132.29 (2F, m), −138.97: −139.13 (2F, m). HRMS for C$_{14}$H$_9$F$_4$NO$_4$S$_2$ [(M−H)$^-$]: calc. 393.9836, found 393.9841.

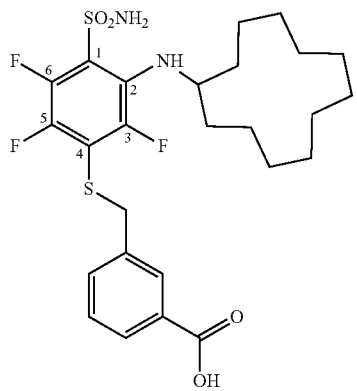 [SMILES: NS(=O)(=O)c1c(F)c(F)c(SCc2cccc(C(=O)O)c2)c(F)c1NC1CCCCCCCCCCC1]

3-[[3-(Cyclododecylamino)-2,5,6-trifluoro-4-sulfamoyl-phenyl]sulfanylmethyl]benzoic acid (MZ21-26)

The mixture of 3-[(2,3,5,6-tetrafluoro-4-sulfamoylphenyl)sulfanylmethyl]benzoic acid (MZ21-24) (0.0413 g, 0.1 mmol), cyclododecylamine (0.03059 g, 0.166 mmol, 1.6 ekv), Et$_3$N (36.3 uL, 0.26 mmol, 2.5 ekv) and 2.5 mL DMSO was heated at 60° C. for 5 days. The mixture was diluted with 10 mL of H$_2$O and acidified to pH=3 with diluted HCl. The resulting mixture was extracted with EtOAc (10 mL×3). The extract was dried over Na$_2$SO$_4$ and concentrated under reduced pressure. The resulting brown residue was subjected to column chromatography silica gel, EtOAc/CHCl$_3$, 1:1, Rf=0.15). Yield: 0.032 g (55%), mp 109-111° C. $^1$H NMR (400 MHz, DMSO-d$_6$, δ): 1.21-1.54 (22H, m, cyclododecane), 3.58 (1H, br s, CH of cyclododecane), 4.28 (2H, s, SCH$_2$), 6.16 (1H, d, J=9 Hz, NH), 7.36-7.45 (2H, m, ArH), 7.81 (2H, d, J=7.5 Hz, ArH), 7.88 (1H, s, ArH) 8.09 (2H, s, SO$_2$NH$_2$), 12.93 (1H, br s, COOH). $^{13}$C NMR (100 MHz, DMSO-d$_6$, δ): 21.02 (cyclododecane), 23.14 (cyclododecane), 23.28 (cyclododecane), 24.09 (cyclododecane), 24.29 (cyclododecane), 30.55 (cyclododecane), 37.80 (SCH$_2$), 52.87 (CH of cyclododecane, d, J=10.8 Hz), 116.69 (C4, dd, $^1$J ($^{19}$F-$^{13}$C)=23.7 Hz, $^2$J ($^{19}$F-$^{13}$C)=19.1 Hz), 119.75 (C1, dd, $^1$J ($^{19}$F-$^{13}$C)=12 Hz, 2J ($^{19}$F-$^{13}$C)=4.7 Hz), 128.83 (Ar), 129.06 (Ar), 130.03 (Ar), 131.52 (Ar), 132.67 (C2, d, $^1$J ($^{19}$F-$^{13}$C)=15.3 Hz), 133.28 (Ar), 138.23 (Ar), 141.64 (C5, ddd, $^1$J ($^{19}$F-$^{13}$C)=237.8 Hz, $^2$J ($^{19}$F-$^{13}$C)=15.7 Hz, $^3$J ($^{19}$F-$^{13}$C)=4.4 Hz), 144.68 (C6, ddd, $^1$J($^{19}$F-$^{13}$C)=249.7 Hz, $^2$J ($^{19}$F-$^{13}$C)=15.3 Hz, $^3$J ($^{19}$F-$^{13}$C)=3.3 Hz), 148.41 (C3, d, $^1$J ($^{19}$F-$^{13}$C)=243 Hz), 167.38 (CO). $^{19}$F NMR (376 MHz, DMSO-d$_6$, δ): -120.27 (1F, d, J=11.28 Hz), -137.18 (1F, dd, $^1$J=27.1, $^2$J=11.7 Hz), -144.84 (1F, dd, $^1$J=26.3 Hz, $^2$J=3.7 Hz). HRMS for C$_{26}$H$_{33}$F$_3$N$_2$O$_4$S$_2$ [(M+H)$^+$]: calc. 559.1907, found 559.1947.

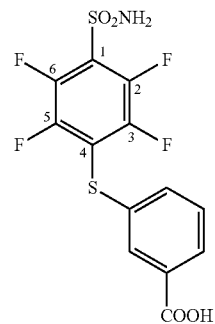 [SMILES: NS(=O)(=O)c1c(F)c(F)c(Sc2cccc(C(=O)O)c2)c(F)c1F]

3-(2,3,5,6-Tetrafluoro-4-sulfamoyl-phenyl)sulfanyl-benzoic acid (MZ21-41)

The mixture of 2,3,4,5,6-pentafluorobenzenesulfonamide (0.15 g, 0.61 mmol), 3-sulfanylbenzoic acid (0.12 g, 0.79 mmol, 1.3 ekv), Et$_3$N (170 uL, 1.21 mmol, 2 ekv) and 8 mL of MeOH was stirred at room temperature for 6 h. The resulting mixture was acidified to pH=3 with diluted HCl. The precipitate was filtered, and recrystallized from MeOH:H$_2$O (2:1). Yield: 0.117 g (50%), mp 243-245° C. $^1$H NMR (400 MHz, DMSO-d$_6$, δ): 7.51 (1H, t, J=7.8 Hz, ArH), 7.68 (1H, d, J=7.6 Hz, ArH), 7.89 (1H, d, J=7.7 Hz, ArH), 7.93 (1H, s, ArH), 8.47 (2H, s, SO$_2$NH$_2$), 13.29 (1H, br s, COOH). $^{13}$C NMR (100 MHz, DMSO-d$_6$, δ): 116.96 (C1, t, J=20 Hz), 124.46 (C4, t, J=16.1 Hz), 129.37 (Ar), 130.55 (Ar), 130.61 (Ar), 132.66 (Ar), 132.86 (Ar), 134.42 (Ar), 143.28 (C2 and C6, dd, $^1$J ($^{19}$F-$^{13}$C)=254.5 Hz, $^2$J ($^{19}$F-$^{13}$C)= 16.6 Hz), 146.9 (C3 and C5, dd, $^1$J ($^{19}$F-$^{13}$C)=249 Hz, $^2$J ($^{19}$F-$^{13}$C)=13.9 Hz), 166.79 (COOH). $^{19}$F NMR (376 MHz, DMSO-d$_6$, δ): -131.90: -132.06 (2F, m), -138.03: -138.20 (2F, m). HRMS for C$_{13}$H$_7$F$_4$NO$_4$S$_2$ [(M-H)$^-$]: calc. 379.9680, found 379.9685.

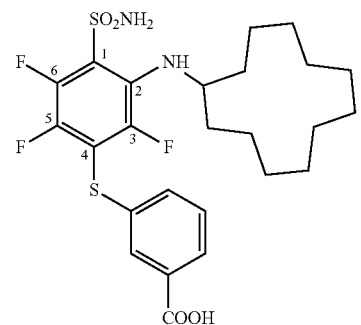 [SMILES: NS(=O)(=O)c1c(F)c(F)c(Sc2cccc(C(=O)O)c2)c(F)c1NC1CCCCCCCCCCC1]

3-[3-(Cyclododecylamino)-2,5,6-trifluoro-4-sulfamoyl-phenyl]sulfanylbenzoic acid (MZ22-07)

The mixture of 3-(2,3,5,6-tetrafluoro-4-sulfamoyl-phenyl)sulfanylbenzoic acid (MZ21-41) (0.1 g, 0.262 mmol), cyclododecylamine (0.077 g, 0.419 mmol, 1.6 ekv), Et$_3$N (95 uL, 0.681 mmol, 2.6 ekv) and 3 mL DMSO was heated at 60° C. for 3 days. The mixture was diluted with 10 mL of H$_2$O and acidified to pH=2 with diluted HCl. The resulting mixture was extracted with EtOAc (10 mL×3). The extract was dried over MgSO$_4$ and concentrated under reduced pressure. The resulting dark yellow oil was subjected to column chromatography (silica gel, CHCl$_3$/MeOH, 8:1, Rf=0.16). Yield: 0.044 g (30%), mp 123-125° C. $^1$H NMR (400 MHz, DMSO-d$_6$, δ): 1.06-1.41 (20H, m, cyclododecane), 1.45-1.59 (2H, m, cyclododecane), 3.55 (1H, br s, NHC<u>H</u>), 6.21 (1H, d, J=8.9 Hz, NH), 7.48 (1H, t, J=7.7 Hz, Ar<u>H</u>), 7.59 (1H, d, J=7.8 Hz, ArH), 7.82-7.88 (1H, m, ArH), 8.21 (2H, br s, SO$_2$NH$_2$), unresolved (1H, br s, COOH). $^{13}$C NMR (100 MHz, DMSO-d$_6$, δ): 21.24 (cyclododecane), 23.21 (cyclododecane), 23.40 (cyclododecane), 23.61 (cyclododecane), 23.84 (cyclododecane), 30.93 (cyclododecane), 52.59 (NHCH, d, J($^{19}$F-$^{13}$C)=10.6 Hz), 116.34 (C4, dd, $^1$J ($^{19}$F-$^{13}$C)=23.7 Hz, $^2$J ($^{19}$F-$^{13}$C)=19 Hz), 120.86 (C1, dd, $^1$J ($^{19}$F-$^{13}$C)=12 Hz, $^2$J ($^{19}$F-$^{13}$C)=4.9 Hz), 128.96 (Ar), 130.15 (Ar), 130.25 (Ar), 133.32 (C2, d, J ($^{19}$F-$^{13}$C)=13.6 Hz), 133.61 (Ar), 133.77 (Ar), 141.36 (C5, ddd, $^1$J ($^{19}$F-$^{13}$C)=240 Hz, $^2$J ($^{19}$F-$^{13}$C)=16.9 Hz, $^3$J ($^{19}$F-$^{13}$C)=3.2 Hz), 143.61 (Ar, overlapped), 144.94 (C6, ddd, $^1$J ($^{19}$F-$^{13}$C)=251 Hz, $^2$J ($^{19}$F-$^{13}$C)=16.3 Hz, $^3$J ($^{19}$F-$^{13}$C)=3.2 Hz), 148.23 (C3, d, $^1$J ($^{19}$F-$^{13}$C)=245 Hz), 167.12 (CO). $^{19}$F NMR (376 MHz, DMSO-d$_6$, δ): -119.15 (1F, d, J=10.5 Hz), -136.14 (1F, dd, $^1$J=27 Hz, $^2$J=11.9 Hz), -144.75 (1F, dd, $^1$J=27 Hz, $^2$J=4.1 Hz). HRMS for C$_{25}$H$_{31}$F$_3$N$_2$O$_4$S$_2$ [(M+H)$^+$]: calc. 545.1750, found 545.1757.

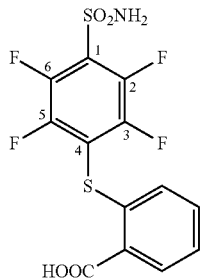 [SMILES: NS(=O)(=O)c1c(F)c(F)c(Sc2ccccc2C(=O)O)c(F)c1F]

2-(2,3,5,6-Tetrafluoro-4-sulfamoyl-phenyl)sulfanyl-benzoic acid (MZ22-08)

The mixture of 2,3,4,5,6-pentafluorobenzenesulfonamide (0.1 g, 0.4 mmol), 2-sulfanylbenzoic acid (0.068 g, 0.44 mmol, 1.1 ekv), Et$_3$N (112 uL, 0.8 mmol, 2 ekv) and 4 mL of MeOH was stirred at room temperature for 6 h. The resulting mixture was acidified to pH=3 with diluted HCl. The white precipitate was filtered, washed with water, dried in air, and subjected to column chromatography (silica gel, EtOAc/MeOH, 4:1, Rf=0.31). Yield: 0.073 g (47%), decomposes at 218° C. $^1$H NMR (400 MHz, DMSO-d$_6$, δ): 6.78 (1H, d, J=7.8 Hz, ArH), 7.21 (1H, t, J=7.3 Hz, ArH), 7.28 (1H, t, J=7 Hz, ArH), 8.01 (1H, d, J=7.1 Hz, ArH), 8.49 (2H, s, SO$_2$NH$_2$), unresolved (1H, br s, COOH). $^{13}$C NMR (100 MHz, DMSO-d$_6$, δ): 118.40 (C1, t, J=24.4 Hz), 124.62 (C4, t, J=15.6 Hz), 125.60 (Ar), 125.70 (Ar), 131.40 (Ar), 131.41 (Ar), 133.77 (Ar), 136.49 (Ar), 143.39 (C2 and C6, dd, $^1$J ($^{19}$F-$^{13}$C)=255.5 Hz, $^2$J ($^{19}$F-$^{13}$C)=17.2 Hz), 147.63 (C3 and C5, dd, $^1$J ($^{19}$F-$^{13}$C)=247.7 Hz, $^2$J ($^{19}$F-$^{13}$C)=13.5 Hz), 170.80 (COOH). $^{19}$F NMR (376 MHz, DMSO-d$_6$, δ): -131.62: -131.77 (2F, m), -137.93: -138.09 (2F, m). HRMS for C$_{13}$H$_7$F$_4$NO$_4$S$_2$ [(M-H)$^-$]: calc. 379.9680, found 379.9686.

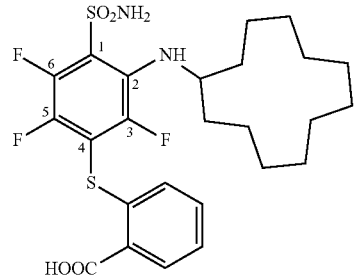 [SMILES: NS(=O)(=O)c1c(F)c(F)c(Sc2ccccc2C(=O)O)c(F)c1NC1CCCCCCCCCCC1]

2-[3-(Cyclododecylamino)-2,5,6-trifluoro-4-sulfamoyl-phenyl]sulfanylbenzoic acid (MZ22-10)

The mixture of 2-(2,3,5,6-tetrafluoro-4-sulfamoyl-phenyl)sulfanylbenzoic acid (MZ22-08), (0.055 g, 0.145 mmol), cyclododecylamine (0.0425 g, 0.232 mmol, 1.6 ekv), Et$_3$N (53 uL, 0.377 mmol, 2.6 ekv) and 3 mL DMSO was heated at 60° C. for 2 days. The mixture was diluted with 10 mL of H$_2$O and acidified to pH=2 with diluted HCl. The resulting mixture was extracted with EtOAc (10 mL×3). The extract was dried over MgSO$_4$ and concentrated under reduced pressure. The resulting dark yellow oil was subjected to column chromatography (silica gel, CHCl$_3$/MeOH, 5:1, Rf=0.18). Yield: 0.013 g (16%), mp 85° C. $^1$H NMR (400 MHz, DMSO-d$_6$, δ): 1.12-1.41 (20H, m, cyclododecane), 1.50-1.62 (2H, m, cyclododecane), 3.64 (1H, br s, NHC<u>H</u>), 6.25 (1H, d, J=8.5 Hz, NH), 6.84 (1H, d, J=7.9 Hz, Ar<u>H</u>) 7.31 (1H, t, J=7.4 Hz, ArH), 7.45 (1H, t, J=7.3 Hz, ArH), 8.0 (1H, d, J=7.4 Hz, ArH), 8.22 (2H, br s, SO$_2$NH$_2$), unresolved (1H, br s, COOH). $^{13}$C NMR (100 MHz, DMSO-d$_6$, δ): 21.22 (cyclododecane), 23.19 (cyclododecane), 23.36 (cyclododecane), 23.76 (cyclododecane), 24.09 (cyclododecane), 30.91 (cyclododecane), 52.75 (NHCH, d, J ($^{19}$F-$^{13}$C)= 10.6 Hz), 116.33 (C4, dd, $^1$J ($^{19}$F-$^{13}$C)=24.3 Hz, $^2$J ($^{19}$F-$^{13}$C)=19.5 Hz), 121.38 (C1, dd, $^1$J ($^{19}$F-$^{13}$C)=11.8 Hz, $^2$J ($^{19}$F-$^{13}$C)=4.9 Hz), 125.64 (Ar), 131.05 (Ar), 131.64 (Ar), 132.37 (Ar), 133.34 (C2, d, J ($^{19}$F-$^{13}$C)=16.4 Hz), 137.67 (Ar), 142.08 (C5, ddd, $^1$J ($^{19}$F-$^{13}$C)=238.9 Hz, $^2$J ($^{19}$F-$^{13}$C)= 15.5 Hz, $^3$J ($^{19}$F-$^{13}$C)=4.2 Hz), 145.08 (C6, ddd, $^1$J ($^{19}$F-$^{13}$C)=250.2 Hz, $^2$J ($^{19}$F-$^{13}$C)=16.4 Hz, $^3$J ($^{19}$F-$^{13}$C)=3.3 Hz), 149.05 (C3, d, J ($^{19}$F-$^{13}$C)=244.7 Hz), 169.00 (CO). $^{19}$F NMR (376 MHz, DMSO-d$_6$, δ): -119.04 (1F, d, J=11.0 Hz), -135.92 (1F, dd, $^1$J=27.8 Hz, $^2$J=12.3 Hz), -143.98 (1F, d, J=26.2 Hz). HRMS for C$_{25}$H$_{31}$F$_3$N$_2$O$_4$S$_2$ [(M+H)$^+$]: calc. 545.1750, found 545.1757.

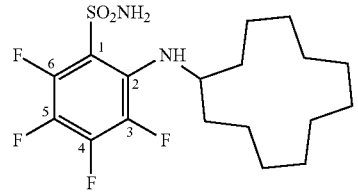 [SMILES: NS(=O)(=O)c1c(F)c(F)c(F)c(F)c1NC1CCCCCCCCCCC1]

2-(Cyclododecylamino)-3,4,5,6-tetrafluoro-benzenesulfonamide (MZ22-25)

The mixture of 2,3,4,5,6-pentafluorobenzenesulfonamide (0.35 g, 1.4 mmol), cyclododecylamine (0.282 g, 1.54 mmol, 1.1 ekv), Et$_3$N (391 uL, 2.8 mmol, 2 ekv), 5 mL of $C_6H_6$ was refluxed for 7 hours. The solvent was evaporated under reduced pressure. The resulting yellow oil was subjected to column chromatography (silica gel, $CHCl_3$, Rf=0.11). Yield: 0.152 g (26%), mp. 133° C. $^1$H NMR (400 MHz, DMSO-$d_6$, δ): 1.14-1.59 (22H, m, cyclodecane), 3.74 (1H, br s, NHC<u>H</u>), 6.46 (1H, d, J=8.9 Hz, NH), 8.18 (2H, s, $SO_2NH_2$). $^{13}$C NMR (100 MHz, DMSO-$d_6$, δ): 21.03 (cyclodecane), 23.13 (cyclodecane), 23.27 (cyclodecane), 24.01 (cyclodecane), 24.23 (cyclodecane), 30.70 (cyclodecane), 52.76 (NHCH, d, J ($^{19}$F-$^{13}$C)=10.4 Hz), 114.74 (C2, d, J ($^{19}$F-$^{13}$C)=10.1 Hz), 131.80 (C3, dt, $^1$J ($^{19}$F-$^{13}$C)=240.1 Hz, $^2$J ($^{19}$F-$^{13}$C)=16.2 Hz), 133.38 (C1, d, J ($^{19}$F-$^{13}$C)=10.9 Hz), 138.00 (C5, ddd, $^1$J ($^{19}$F-$^{13}$C)=243.7 Hz, $^2$J ($^{19}$F-$^{13}$C)=12.5 Hz, $^3$J ($^{19}$F-$^{13}$C)=3.0 Hz), 141.20 (C6, d, J ($^{19}$F-$^{13}$C)=227.3 Hz), 145.83 (C4, ddd, $^1$J ($^{19}$F-$^{13}$C)=245.6 Hz, $^2$J ($^{19}$F-$^{13}$C)=12.4 Hz, 3J($^{19}$F-$^{13}$C)=4.3 Hz). $^{19}$F NMR (376 MHz, DMSO-$d_6$, δ): −135.84 (1F, dt, J=25.7 Hz, $^2$J=7.2 Hz), −151.68 (1F, td, J=22.3 Hz, $^2$J=6.5 Hz), −154.44 (1F, d, J=21.2 Hz), −172.73 (1F, td, $^1$J=25.5 Hz, $^2$J=5.1 Hz). HRMS for $C_{18}H_{27}F_4N_2O_2S$ [(M+H)$^+$]: calc. 411.1724, found 411.1727.

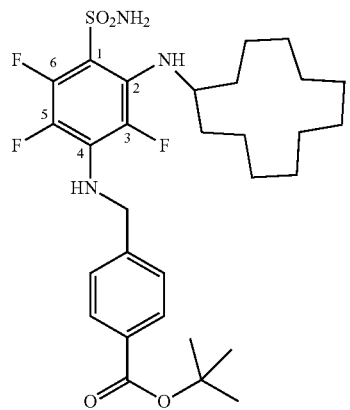 [SMILES: CC(C)(C)OC(=O)c1ccc(CNc2c(F)c(F)c(S(N)(=O)=O)c(NC3CCCCCCCCCCC3)c2F)cc1]

tert-Butyl-4-[[3-(cyclododecylamino)-2,5,6-trifluoro-4-sulfamoyl-anilino]methyl]benzoate (MZ22-27)

The mixture of 2-(cyclododecylamino)-3,4,5,6-tetrafluoro-benzenesulfonamide (MZ22-25), (0.074 g, 0.18 mmol), tert-butyl 4-(aminomethyl)benzoate (0.041 g, 0.2 mmol, 1.1 ekv), $Et_3N$ (50 uL, 0.36 mmol, 2 ekv) and 1 mL DMSO was heated at 60° C. for 28 hours. The mixture was diluted with 10 mL of $H_2O$. The resulting mixture was extracted with EtOAc (10 mL×3). The extract was dried over $MgSO_4$ and concentrated under reduced pressure. The resulting yellow oil was subjected to column chromatography (silica gel, $CH_2Cl_2$:EtOAc (30:1), Rf=0.26). Yield: 0.033 g (29%), mp 224-226° C. $^1$H NMR (400 MHz, DMSO-$d_6$, δ): 1.13-1.48 (22H, m, cyclododecane), 1.52 (9H, s, $CH_3$), 3.48 (1H, br s, NH<u>CH</u>), 4.54 (2H, d, J=6.4 Hz, <u>NHCH</u>$_2$), 5.96 (1H, d, J=9.2 Hz, <u>NHCH</u>), 6.92 (1H, br s, N<u>HCH</u>$_2$), 7.37 (2H, d, J=8.1 Hz, ArH), 7.67 (2H, s, $SO_2NH_2$), 7.84 (2H, d, J=8.2 Hz, ArH). $^{13}$C NMR (100 MHz, DMSO-$d_6$, δ): 21.26 (cyclododecane), 23.25 (cyclododecane), 23.42 (cyclododecane), 23.71 (cyclododecane), 24.01 (cyclododecane), 28.23 ($CH_3$), 30.73 (cyclododecane), 47.77 (NHCH$_2$), 52.42 (NHCH, d, J ($^{19}$F-$^{13}$C)=10.7 Hz), 80.93 (C(CH$_3$)$_3$), 107.36 (C2, dd, $^1$J ($^{19}$F-$^{13}$C)=11.9 Hz, $^2$J ($^{19}$F-$^{13}$C)=3.6 Hz), 126.92 (Ar), 129.63 (Ar), 130.39 (Ar), 130.82 (C1, dd, $^1$J ($^{19}$F-$^{13}$C)=10 Hz, $^2$J ($^{19}$F-$^{13}$C)=4.9 Hz), 132.87 (C4, d, J ($^{19}$F-$^{13}$C)=11.9 Hz), 133.4 (C5, dm, $^1$J ($^{19}$F-$^{13}$C)=243.1 Hz), 137.83 (C3, dd, $^1$J ($^{19}$F-$^{13}$C)=234.1 Hz, $^2$J ($^{19}$F-$^{13}$C)=5.1 Hz), 145.86 (C6, ddd, $^1$J ($^{19}$F-$^{13}$C)=244 Hz, $^2$J ($^{19}$F-$^{13}$C)=12.8 Hz, $^3$J ($^{19}$F-$^{13}$C)=2.4 Hz), 145.96 (Ar), 165.20 (CO). $^{19}$F NMR (376 MHz, DMSO-$d_6$, δ): −139.49 (1F, dd, $^1$J=24.2 Hz, $^2$J=7.4 Hz), −147.68 (1F, s), −167.65 (1F, d, J=24.2 Hz). HRMS for $C_{30}H_{43}F_3N_3O_4S$ [(M+H)$^+$]: calc. 598.2921, found 598.2943.

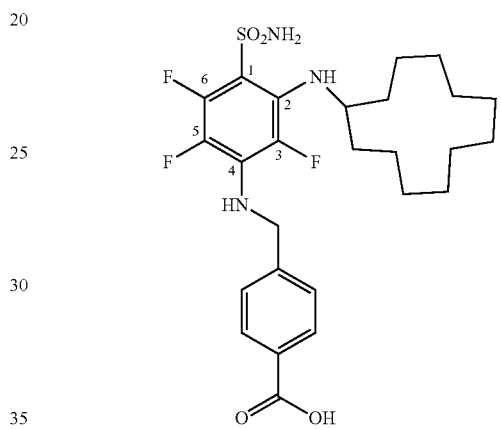

4-[[3-(Cyclododecylamino)-2,5,6-trifluoro-4-sulfamoyl-anilino]methyl]benzoic acid (MZ22-28)

The mixture of tert-Butyl-4-[[3-(cyclododecylamino)-2,5,6-trifluoro-4-sulfamoyl-anilino]methyl]benzoate (MZ22-27) (0.033 g, 0.055 mmol), 0.6 mL TFA was stirred at room temperature for 4 val. The solvent was evaporated under reduced pressure, the yellow oil was obtained. Yield: 0.026 g (86%). $^1$H NMR (400 MHz, DMSO-$d_6$, δ): 1.14-1.53 (22H, m, cyclododecane), 3.74 (1H, br s, NH<u>CH</u>), 4.55 (2H, d, J=6.4 Hz, NH<u>CH</u>$_2$), 5.96 (1H, br s, <u>NHCH</u>), 6.92 (1H, br s, <u>NHCH</u>$_2$), 7.37 (2H, d, J=8 Hz, ArH), 7.67 (2H, s, $SO_2NH_2$), 7.89 (2H, d, J=8.1 Hz, ArH). $^{13}$C NMR (100 MHz, DMSO-$d_6$, δ): 21.30 (cyclododecane), 23.26 (cyclododecane), 23.43 (cyclododecane), 23.70 (cyclododecane), 24.00 (cyclododecane), 30.78 (cyclododecane), 47.77 (NHCH$_2$), 52.42 (NHCH, d, J($^{19}$F-$^{13}$C)=11 Hz), 107.25 (C1, dd, $^1$J ($^{19}$F-$^{13}$C)=11.1 Hz, $^2$J($^{19}$F-$^{13}$C)=2.9 Hz), 127.01 (Ar), 129.82 (Ar), 130.03 (Ar), 130.76 (C4, d, J ($^{19}$F-$^{13}$C)=10.2 Hz), 132.83 (C2, d, J ($^{19}$F-$^{13}$C)=12.4 Hz), 137.80 (C3, dd, $^1$J($^{19}$F-$^{13}$C)=234.9 Hz, $^2$J($^{19}$F-$^{13}$C)=6.4 Hz), 145.93 (C6, d, J ($^{19}$F-$^{13}$C)=235.1 Hz), 145.99 (Ar), 167.56 (CO), not found (C5). $^{19}$F BMR (376 MHz, DMSO-$d_6$, δ): −139.40 (1F, dd, J=24.1 Hz, $^2$J=6.8 Hz), −147.84 (1F, s), −167.80 (1F, d, J=23.9 Hz). HRMS for $C_{26}H_{35}F_3N_3O_4S$ [(M+H)$^+$]: calc. 542.2295, found 542.2291.

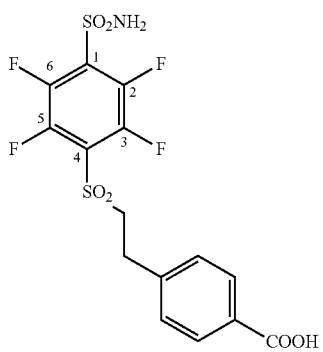 [SMILES: NS(=O)(=O)c1c(F)c(F)c(S(=O)(=O)CCc2ccc(C(=O)O)cc2)c(F)c1F]

4-[2-(2,3,5,6-Tetrafluoro-4-sulfamoyl-phenyl)sulfonylethyl]benzoic acid (MZ20-06)

The mixture of 4-[2-(2,3,5,6-tetrafluoro-4-sulfamoyl-phenyl)sulfanylethyl]benzoic acid (0.1 g, 0.24 mmol) and 5 mL AcOH was heated in an oil bath at 70° C. 100 uL of hydrogen peroxide (30%) was poured in to the reaction mixture every 15 minutes. The reaction was stopped after pouring a total of 2.4 mL of hydrogen peroxide. The solvent was removed by evaporation under reduced pressure. Yield: 0.096 g (89%), decomposes at 303° C. $^1$H NMR (400 MHz, DMSO-d$_6$, δ): 3.16 (2H, d, J=8 Hz, SO$_2$CH$_2$CH$_2$), 3.98 (2H, d, J=7.7 Hz, SO$_2$CH$_2$CH$_2$), 7.43 (2H, d, J=8 Hz, ArH), 7.84 (2H, d, J=8 Hz, ArH), 8.63 (2H, s, SO$_2$NH$_2$), 12.89 (1H, s, ArCOOH). $^{13}$C NMR (100 MHz, DMSO-d$_6$, δ): 27.86 (SO$_2$CH$_2$CH$_2$), 57.31 (SO$_2$CH$_2$CH$_2$), 120.98 (C1, t, J ($^{19}$F-$^{13}$C)=14.8 Hz), 128.17 (C4, t, J ($^{19}$F-$^{13}$C)=15.6 Hz), 129.30 (Ar), 129.77 (Ar), 129.98 (Ar), 142.80 (Ar), 143.56 (C2 and C6, dd, $^1$J ($^{19}$F-$^{13}$C)=256.5 Hz, $^2$J ($^{19}$F-$^{13}$C)=17.1 Hz), 144.87 (C3 and C5, dd, $^1$J ($^{19}$F-$^{13}$C)=258.5 Hz, $^2$J ($^{19}$F-$^{13}$C)= 16.3 Hz), 167.54 (CO). $^{19}$F NMR (376 MHz, DMSO-d$_6$, δ): −135.39: −135.57 (2F, m), −136.45: −136.63 (2F, m)). HRMS for C$_{15}$H$_{11}$F$_4$NO$_4$S$_2$[(M−H)$^−$]: calc. 407.9993, found 407.9997.

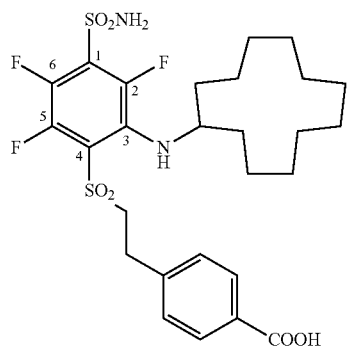 [SMILES: NS(=O)(=O)c1c(F)c(F)c(S(=O)(=O)CCc2ccc(C(=O)O)cc2)c(NC2CCCCCCCCCCC2)c1F]

4-[2-[2-(Cyclododecylamino)-3,5,6-trifluoro-4-sulfamoyl-phenyl]sulfonylethyl]benzoic acid (MZ21-03)

The mixture of 4-(2-((2,3,5,6-tetrafluoro-4-sulfamoylphenyl)sulfonyl)ethyl)benzoic acid (MZ20-06) (0.1047 g, 0.23 mmol), cyclododecylamine (0.1 g, 0.54 mmol, 2.3 ekv) and 3 mL DMSO was stirred at room temperature for 28 h. The mixture was diluted with 10 mL of H$_2$O and acidified to pH=4 with diluted HCl. The resulting mixture was extracted with EtOAc (10 mL×3). The extract was dried over Na$_2$SO$_4$ and concentrated under reduced pressure. The resulting brown oil was subjected to column chromatography (silica gel, EtOAc/CHCl$_3$, 3:1, Rf=0.37). Yield: 0.021 g (14%), decomposes at 230-231° C. $^1$H NMR (400 MHz, DMSO-d$_6$, δ): 1.06-1.70 (22H, m, cyclododecane), 3.13 (2H, t, J=8 Hz, SCH$_2$CH$_2$), 3.78 (1H, br s, CH of cyclododecane) 3.90 (2H, t, J=7.4 Hz, SCH$_2$CH$_2$), 6.52 (1H, d, J=8.6 Hz, NH), 7.41 (2H, d, J=8 Hz, ArH), 7.85 (2H, d, J=8 Hz, ArH), 8.33 (2H, s, SO$_2$NH$_2$), 12.86 (1H, br s, COOH). $^{13}$C NMR (100 MHz, DMSO-d$_6$, δ): 20.93 (cyclododecane), 23.05 (cyclododecane), 23.16 (cyclododecane), 24.28 (cyclododecane), 24.45 (cyclododecane), 27.95 (SO$_2$CH$_2$CH$_2$), 30.53 (cyclododecane), 53.34 (CH of cyclododecane, d, J($^{19}$F-$^{13}$C)=11.6 Hz), 57.27 (SO$_2$CH$_2$CH$_2$), 115.08 (C4, dd, $^1$J ($^{19}$F-$^{13}$C)=12.6 Hz, $^2$J ($^{19}$F-$^{13}$C)=5.2 Hz), 128.03 (C1, dd, $^1$J ($^{19}$F-$^{13}$C)=18.2 Hz, $^2$J ($^{19}$F-$^{13}$C)=13.8 Hz), 129.17 (Ar), 129.76 (Ar), 129.83 (Ar), 135.71 (C3, d, J ($^{19}$F-$^{13}$C)=12.4 Hz), 137.32 (C6, ddd, $^1$J ($^{19}$F-$^{13}$C)=248.3 Hz, 2J ($^{19}$F-$^{13}$C)=16.4 Hz, $^3$J ($^{19}$F-$^{13}$C)=3.8 Hz), 142.89 (Ar), 144.54 (C2, d, J($^{19}$F-$^{13}$C)=256 Hz), 146.10 (C5, dd, $^1$J ($^{19}$F-$^{13}$C)=256.1 Hz, $^2$J ($^{19}$F-$^{13}$C)=16 Hz), 167.54 (CO). $^{19}$F NMR (376 MHz, DMSO-d$_6$, δ): −124.88 (1F, d, J=7.7 Hz), −133.94 (1F, dd, J=27.1 Hz, $^2$J=12.4 Hz), −150.32 (1F, dd, J=26.3 Hz, $^2$J=6.4 Hz). HRMS for C$_{27}$H$_{35}$F$_3$N$_2$O$_6$S$_2$ [(M+H)$^+$]: calc. 605.1961, found 412.1222. HRMS for C$_{27}$H$_{35}$F$_3$N$_2$O$_6$S$_2$ [(M+H)$^+$]: calc. 605.1961, found 605.1958.

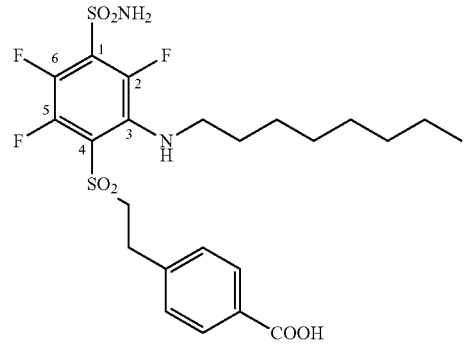 [SMILES: CCCCCCCCNc1c(F)c(S(N)(=O)=O)c(F)c(F)c1S(=O)(=O)CCc1ccc(C(=O)O)cc1]

4-[2-[2,3,5-Trifluoro-6-(octylamino)-4-sulfamoyl-phenyl]sulfonylethyl]benzoic acid (MZ21-04)

The mixture of 4-(2-((2,3,5,6-tetrafluoro-4-sulfamoylphenyl)sulfonyl)ethyl)benzoic acid (MZ20-06) (0.065 g, 0.15 mmol), octylamine (50 μL, 0.3 mmol, 2 ekv) and 3 mL DMSO was stirred at room temperature for 18 h. The mixture was diluted with 10 mL of H$_2$O and acidified to pH=4 with diluted HCl. The resulting mixture was extracted with EtOAc (10 mL×3). The extract was dried over Na$_2$SO$_4$ and concentrated under reduced pressure. The resulting brown oil was subjected to column chromatography (silica gel, CHCl$_3$/MeOH, 4:1, Rf=0.42). Yield: 0.011 g (13%), decomposes at 231° C. $^1$H NMR (400 MHz, DMSO-d$_6$, δ): 0.80-0.90 (3H, m, octane), 1.15-1.41 (10H, m, octane), 1.51-1.60 (2H, m, octane), 3.08 (2H, t, J=6.7 Hz, SO$_2$CH$_2$CH$_2$), 3.27 (2H, p, J=6.3 Hz, NHCH$_2$) 3.92 (2H, t, J=6.7 Hz, SO$_2$CH$_2$), 6.56 (1H, br s, NH), 7.05 (2H, d, J=7.7 Hz, ArH), 7.58 (2H, d, J=7.7 Hz, ArH), 9.15 (3H, br s, SO$_2$NH$_2$ and COOH). $^{13}$C NMR (100 MHz, DMSO-d$_6$, δ):

14.40 (octane), 22.53 (octane), 24.55 (SO$_2$CH$_2$CH$_2$), 26.65 (octane), 28.84 (octane), 29.09 (octane), 30.47 (octane, d, J ($^{19}$F-$^{13}$C)=3 Hz), 31.65 (octane), 46.64 (NHCH$_2$, d, J ($^{19}$F-$^{13}$C)=12.2 Hz), 57.21 (SO$_2$CH$_2$), 113.89 (C4, dd, $^1$J ($^{19}$F-$^{13}$C)=12.8 Hz, $^2$J ($^{19}$F-$^{13}$C)=5.3 Hz), 127.51 (Ar), 128.74 (C1, dd, $^1$J ($^{19}$F-$^{13}$C)=18.8 Hz, $^2$J ($^{19}$F-$^{13}$C)=15.8 Hz), 129.08 (Ar), 136.01 (C3, d, J ($^{19}$F-$^{13}$C)=14.6 Hz), 136.70 (C6, ddd, $^1$J ($^{19}$F-$^{13}$C)=244 Hz, $^2$J ($^{19}$F-$^{13}$C)=19.7 Hz, $^3$J ($^{19}$F-$^{13}$C)=5.7 Hz), 137.70 (Ar), 138.81 (Ar), 144.20 (C2, d, J ($^{19}$F-$^{13}$C)=253.2 Hz), 145.44 (C5, dd, $^1$J ($^{19}$F-$^{13}$C)=251 Hz, $^2$J ($^{19}$F-$^{13}$C)=9.8 Hz), 171.15 (CO). $^{19}$F NMR (376 MHz, DMSO-d$_6$, δ): −126.43 (1F, s), −135.48 (1F, dd, $^1$J=26.9 Hz, $^2$J=11.8 Hz), −151.67 (1F, d, $^1$J=26.8 Hz). HRMS for C$_{23}$H$_{29}$F$_3$N$_2$O$_6$S$_2$ [(M+H)$^+$]: calc. 551.1492, found 551.1515.

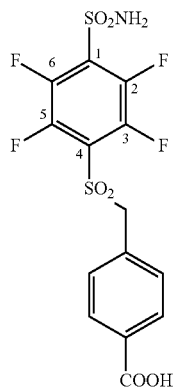 [SMILES: NS(=O)(=O)c1c(F)c(F)c(S(=O)(=O)Cc2ccc(C(=O)O)cc2)c(F)c1F]

4-[(2,3,5,6-tetrafluoro-4-sulfamoyl-phenyl)sulfonylmethyl]benzoic acid (MZ21-20)

4-((2,3,5,6-tetrafluoro-4-sulfamoylphenyl)sulfanylmethyl)benzoic acid (0,113 g, 0.285 mmol) and acetic acid (5 mL) was stirred and heated at 70° C. 30% hydrogen peroxide solution was added to the reaction mixture (200 uL every 5 minutes) after a total of 2.4 mL was added, then the mixture was stirred for another 2 hours. The mixture was allowed to cool to room temperature. The precipitated product was filtered off and dried in air. Yield: 0.072 g (59%), decomposes at 317° C. $^1$H NMR (400 MHz, DMSO-d$_6$, δ): 5.10 (2H, s, SO$_2$CH$_2$), 7.47 (2H, d, J=7.4 Hz, ArH), 7.94 (2H, d, J=7.5 Hz, ArH), 8.66 (2H, s, SO$_2$NH$_2$), 13.14 (1H, br s, COOH). $^{13}$C NMR (100 MHz, DMSO-d$_6$, δ): 62.66 (SO$_2$CH$_2$), 120.27 (C1, t, J($^{19}$F-$^{13}$C)=15 Hz), 128.49 (C4, t, $^1$J ($^{19}$F-$^{13}$C)=15 Hz), 129.89 (Ar), 131.84 (Ar), 131.94 (Ar), 132.06 (Ar), 143.28 (C2 and C6, dd, $^1$J ($^{19}$F-$^{13}$C)=261 Hz, $^2$J ($^{19}$F-$^{13}$C)=13.7 Hz), 144.86 (C3 and C5, dd, $^1$J($^{19}$F-$^{13}$C)=262.6 Hz, $^2$J ($^{19}$F-$^{13}$C)=12.6 Hz), 167.34 (CO). $^{19}$F NMR (376 MHz, DMSO-d$_6$, δ): −134.62: −134.99 (2F, m), −136.40-136.71 (2F, m). HRMS for C$_{14}$H$_9$F$_4$NO$_4$S$_2$ [(M−H)$^−$]: calc. 393.9836, found 393.9840.

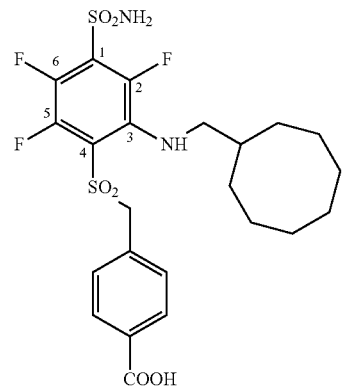 [SMILES: NS(=O)(=O)c1c(F)c(F)c(S(=O)(=O)Cc2ccc(C(=O)O)cc2)c(NCC2CCCCCCC2)c1F]

4-[[2-(Cyclooctylmethylamino)-3,5,6-trifluoro-4-sulfamoyl-phenyl]sulfonylmethyl]benzoic acid (MZ21-39)

The mixture of 4-(((2,3,5,6-tetrafluoro-4-sulfamoylphenyl)sulfonyl)methyl)benzoic acid (MZ21-20) (0.072 g, 0.168 mmol), cyclooctylmethanamine (0.0475 g, 0.336 mmol, 2 ekv) and 3 mL of DMSO was stirred at room temperature for 25 hours. The mixture was diluted with 10 mL of H$_2$O and acidified to pH=2 with diluted HCl. The resulting mixture was extracted with EtOAc (10 mL×3). The extract was dried over MgSO$_4$ and concentrated under reduced pressure. The resulting dark greenish oil was subjected to column chromatography (silica gel, CHCl$_3$/MeOH, 4:1, Rf=0.28). Yield: 0.021 g (22%), decomposes at 229-230° C. $^1$H NMR (400 MHz, DMSO-d$_6$, δ): 1.03-1.67 (15H, m, cyclooctane), 2.73 (2H, q, J=5.5 Hz, NHCH$_2$), 5.00 (2H, s, SO$_2$CH$_2$), 6.18 (1H, s, NH), 7.39 (2H, d, J=8.1 Hz, ArH), 7.93 (2H, d, J=8.1 Hz, ArH), 8.34 (2H, s, SO$_2$NH$_2$), 13.11 (1H, br s, COOH). $^{13}$C NMR (100 MHz, DMSO-d$_6$, δ): 25.19 (cyclooctane), 26.21 (cyclooctane), 26.88 (cyclooctane), 29.81 (cyclooctane), 38.29 (CH of cyclooctane, d, J ($^{19}$F-$^{13}$C)=2 Hz), 53.46 (NHCH$_2$, d, J($^{19}$F-$^{13}$C)=11.5 Hz), 62.35 (SO$_2$CH$_2$), 113.10 (C1, dd, J($^{19}$F-$^{13}$C)=13.4 Hz, $^2$J ($^{19}$F-$^{13}$C)=5.4 Hz), 128.40 (C4, dd, $^1$J ($^{19}$F-$^{13}$C)=17.8 Hz, $^2$J ($^{19}$F-$^{13}$C)=14.3 Hz), 129.89 (Ar), 131.79 (Ar), 131.87 (Ar), 132.57 (Ar), 136.77 (C5, ddd, $^1$J ($^{19}$F-$^{13}$C)=245 Hz, $^2$J ($^{19}$F-$^{13}$C)=16.2 Hz, $^3$J ($^{19}$F-$^{13}$C)=3.6 Hz), 137.21 (C2, d, J ($^{19}$F-$^{13}$C)=12.9 Hz), 143.92 (C3, d, J($^{19}$F-$^{13}$C)=253.9 Hz), 145.92 (C6, ddd, J($^{19}$F-$^{13}$C)=254.3 Hz, $^2$J ($^{19}$F-$^{13}$C)=15.9 Hz, $^3$J ($^{19}$F-$^{13}$C)=4.1 Hz), 167.26 (CO). $^{19}$F NMR (376 MHz, DMSO-d$_6$, δ): −125.60 (1F, s), −133.67 (1F, dd, $^1$J=27.1 Hz, $^2$J=12.2 Hz), −151.06 (1F, dd, $^1$J=27.1 Hz, $^2$J=7.2 Hz). HRMS for C$_{23}$H$_{27}$F$_3$N$_2$O$_6$S$_2$ [(M+H)$^+$]: calc. 549.1335, found 549.1327.

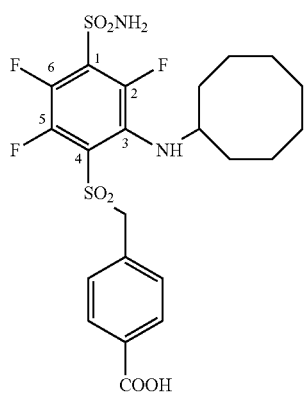 [SMILES: NS(=O)(=O)c1c(F)c(F)c(S(=O)(=O)Cc2ccc(C(=O)O)cc2)c(NC2CCCCCCC2)c1F]

4-[[2-(Cyclooctylamino)-3,5,6-trifluoro-4-sulfamoyl-phenyl]sulfonylmethyl]benzoic acid (MZ21-22)

The mixture of 4-(((2,3,5,6-tetrafluoro-4-sulfamoylphenyl)sulfonyl)methyl)benzoic acid (MZ21-20) (0.024 g, 0.056 mmol), cyclooctylamine (15 μL, 0.11 mmol, 2 ekv) and 3 mL of DMSO was stirred at room temperature for 22 hours. The mixture was diluted with 10 mL of H$_2$O and acidified to pH=2 with diluted HCl. The resulting mixture was extracted with EtOAc (10 mL×3). The extract was dried over MgSO$_4$ and concentrated under reduced pressure. The resulting greenish oil was subjected to column chromatography (silica gel, CHCl$_3$/MeOH, 4:1, Rf=0.28). Yield: 0.013 g (41%), decomposes at 196° C. $^1$H NMR (400 MHz, DMSO-d$_6$, δ): 1.03-1.62 (14H, m, cyclooctane), 3.53 (1H, br s, NHCH), 5.00 (2H, s, SO$_2$CH$_2$), 6.33 (1H, s, NHCH), 7.38 (2H, d, J=8.0 Hz, ArH), 7.92 (2H, d, J=8.1 Hz, ArH), 8.37 (2H, s, SO$_2$NH$_2$), 13.17 (1H, br s, COOH). $^{13}$C NMR (100 MHz, DMSO-d$_6$, δ): 23.10 (cyclooctane), 25.27 (cyclooctane), 27.02 (cyclooctane), 32.34 (cyclooctane), 55.62 (CH of cyclooctane, d, J($^{19}$F-$^{13}$C)=11.4 Hz), 62.38 (SO$_2$CH$_2$), 113.49 (C1, dd, J($^{19}$F-$^{13}$C)=14 Hz, 2J($^{19}$F-$^{13}$C)=5.1 Hz), 128.25 (C4, dd, J($^{19}$F-$^{13}$C)=18.1 Hz, $^2$J ($^{19}$F-$^{13}$C)=14.0 Hz), 129.92 (Ar), 131.85 (Ar), 131.97 (Ar), 132.53 (Ar), 135.67 (C2, d, J ($^{19}$F-$^{13}$C)=13 Hz), 137.02 (C5, ddd, $^1$J ($^{19}$F-$^{13}$C)= 224 Hz, $^2$J ($^{19}$F-$^{13}$C)=16.7 Hz, $^3$J ($^{19}$F-$^{13}$C)=3.8 Hz), 144.07 (C3, d, $^1$J ($^{19}$F-$^{13}$C)=254.4 Hz, 145.94 (C6, ddd, $^1$J ($^{19}$F-$^{13}$C)=223 Hz, $^2$J ($^{19}$F-$^{13}$C)=16.3 Hz, $^3$J ($^{19}$F-$^{13}$C)=4.3 Hz), 167.26 (CO). $^{19}$F NMR (376 MHz, DMSO-d$_6$, δ): −125.28 (1F, s), −133.16 (1F, dd, J=27.2 Hz, $^2$J=12.5 Hz), −151.06 (1F, dd, $^1$J=27.2 Hz, $^2$J=6.6 Hz). HRMS for C$_{22}$H$_{26}$F$_3$N$_2$O$_6$S$_2$ [(M+H)$^+$]: calc. 535.1179, found 535.1127.

Evaluation of the Anti-Aggregation Properties of Target Compounds

The anti-aggregation properties of the target compounds were tested on amyloid-beta—a 42 amino acid peptide, associated with the onset and progression of one of the most widespread neurodegenerative disorders—Alzheimer's disease. Since the general steps of amyloid formation apply to most amyloidogenic proteins/peptides, if the target compounds can influence the aggregation rate of amyloid-beta, then it is possible that they would also affect a variety of other aggregate-forming proteins/peptides.

The biosynthesis and purification of amyloid-beta peptide were performed following the procedure described in the literature (Šneideris, T. et al. Peer J. 3:e1271 (2015)). The purified peptide fractions (20 mM phosphate buffer solution containing 0.2 mM EDTA and 0.02% NaN$_3$, pH 8.0) were mixed with 20 mM sodium phosphate buffer containing 0.2 mM EDTA and 0.02% NaN$_3$ (pH 6.33), 10 mM ThT stock solution, and 10 mM of selected inhibitor compound dissolved in DMSO to yield 1 μM Aβ42, 20 μM ThT and 25 μM inhibitor compound in a phosphate buffer solution containing the same amount of EDTA and NaN$_3$ (pH 7.0). The aggregation kinetics were followed in 96-well plates (Fisher, cat. No. 10438082) (sample volume was 80 μL) at 37° C. by measuring ThT fluorescence using 440 nm excitation and 480 emission wavelengths in a ClarioStar Plus (BMG Labtech, Ortenberg, Germany).

The invention claimed is:
1. A composition for treatment of an illness related to amyloid aggregation, wherein the composition comprises an effective amount of a fluorinated benzensulfonamide compound as part of a pharmaceutical formulation, wherein the fluorinated benzensulfonamide compound is of structure I or a pharmaceutically acceptable salt thereof:

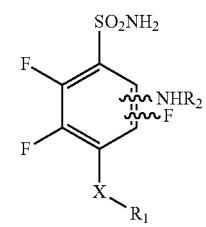

wherein X is S, NH or SO$_2$;
NHR$_2$ and F are at ortho and meta positions with respect to the sulfonamide group, such that
when X=S or NH, NHR$_2$ is at ortho position and F is at meta position, and when X=SO$_2$,
NHR$_2$ is at meta position and F is at ortho position;
R$_1$ is selected from the group consisting of:

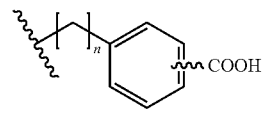

wherein n=0, 1, or 2, and COOH is at the position ortho, meta, or para, as shown:

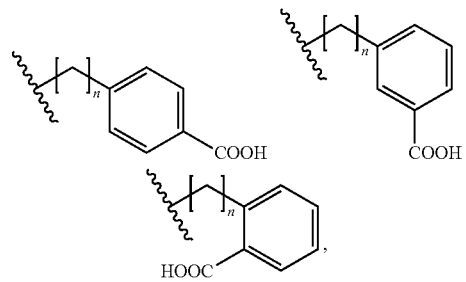

benzene-dicarboxylic acid, wherein n=0, 1, or 2, and COOH groups are at different positions of benzene ring, as shown:

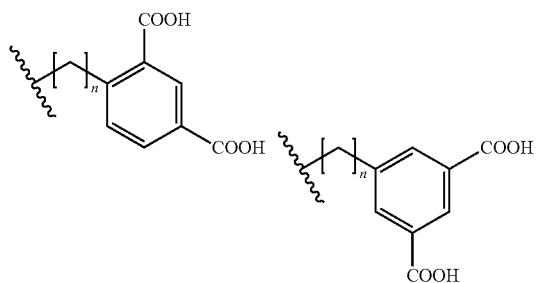

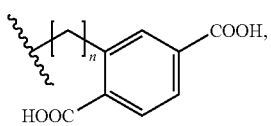

and
2-phenylacetic acid, as shown:

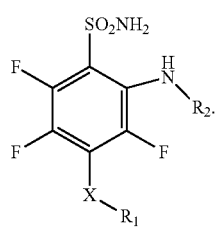

R₂ is cycloalkyl wherein cycloalkyl comprises cycloalkanes from cyclooctane to cyclotetradecane (C8-C14), cycloalkylmethyl wherein cycloalkyl comprises cycloalkanes from cyclohexane to cyclododecane (C6-C12), alkyl where alkyl comprises alkanes from hexane to tetradecane (C6-C14), or alkyl where alkyl comprises branched alkanes from C6 to C14.

2. The composition according to claim 1, wherein the fluorinated benzensulfonamide compound is of structure Ia, wherein X=S or NH, NHR₂ is at the ortho position, and F is at the meta position, as shown:

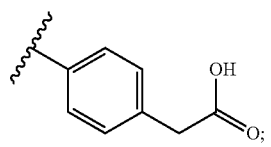 [SMILES: *c1ccc(CC(=O)O)cc1]

3. The composition according to claim 1, wherein the fluorinated benzensulfonamide compound is of structure Ib, wherein X=SO₂, NHR₂ is at the meta position, and F is at the ortho position

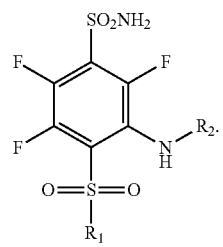

4. The composition according to claim 1, wherein the fluorinated benzensulfonamide compound is selected from the group consisting of:

4-[2-[3-(cyclooctylamino)-2,5,6-trifluoro-4-sulfamoyl-phenyl]sulfanylethyl]benzoic acid, 4-[2-[3-(cyclododecylamino)-2,5,6-trifluoro-4-sulfamoyl-phenyl]sulfanylethyl]benzoic acid, 4-[2-[2,3,6-trifluoro-5-(hexylamino)-4-sulfamoyl-phenyl]sulfanylethyl]benzoic acid, 4-[2-[2,3,6-trifluoro-5-(heptylamino)-4-sulfamoyl-phenyl]sulfanylethyl]benzoic acid, 4-[2-[2,3,6-trifluoro-5-(octylamino)-4-sulfamoyl-phenyl]sulfanylethyl]benzoic acid, 4-[2-[2,3,6-trifluoro-5-(nonylamino)-4-sulfamoyl-phenyl]sulfanylethyl]benzoic acid, 4-[[3-(cyclodecylamino)-2,5,6-trifluoro-4-sulfamoyl-phenyl]sulfanylmethyl]benzoic acid, 4-[[3-(cyclododecylamino)-2,5,6-trifluoro-4-sulfamoyl-phenyl]sulfanylmethyl]benzoic acid, 4-[[3-(cyclooctylmethylamino)-2,5,6-trifluoro-4-sulfamoyl-phenyl]sulfanylmethyl]benzoic acid, 4-[[2,3,6-trifluoro-5-(3-propylhexylamino)-4-sulfamoyl-phenyl]sulfanylmethyl]benzoic acid, 4-[[3-(3,4-dimethylhexylamino)-2,5,6-trifluoro-4-sulfamoyl-phenyl]sulfanylmethyl]benzoic acid, 4-[3-(cyclododecylamino)-2,5,6-trifluoro-4-sulfamoyl-phenyl]sulfanylbenzoic acid, 2-[4-[3-(cyclododecylamino)-2,5,6-trifluoro-4-sulfamoyl-phenyl]sulfanylphenyl]acetic acid, 3-[[3-(cyclododecylamino)-2,5,6-trifluoro-4-sulfamoylphenyl]sulfanylmethyl]benzoic acid, 3-[3-(cyclododecylamino)-2,5,6-trifluoro-4-sulfamoyl-phenyl]sulfanylbenzoic acid, 2-[3-(cyclododecylamino)-2,5,6-trifluoro-4-sulfamoyl-phenyl]sulfanylbenzoic acid, 4-[[3-(cyclododecylamino)-2,5,6-trifluoro-4-sulfamoyl-anilino]methyl]benzoic acid, 4-[2-[2-(cyclododecylamino)-3,5,6-trifluoro-4-sulfamoyl-phenyl]sulfonylethyl]benzoic acid, 4-[2-[2,3,5-trifluoro-6-(octylamino)-4-sulfamoyl-phenyl]sulfonylethyl]benzoic acid, 4-[[2-(cyclooctylmethylamino)-3,5,6-trifluoro-4-sulfamoyl-phenyl]sulfonylmethyl]benzoic acid, and 4-[[2-(cyclooctylamino)-3,5,6-trifluoro-4-sulfamoyl-phenyl]sulfonylmethyl]benzoic acid.

5. A composition as part of a pharmaceutical formulation according to claim 1,
   wherein the compound is administered with pharmaceutically acceptable diluents, excipient, or carrier.

6. A composition as part of a pharmaceutical formulation according to claim 1,
   wherein the pharmaceutical composition is effective at inhibiting an amyloid aggregation process, wherein the amyloid aggregation process occurs in any amyloidogenic protein from the group of: beta amyloid peptide, alpha-synuclein, prion protein, Tau protein, superoxide dismutase 1, islet amyloid polypeptide, insulin, and lysozyme.

7. A method to treat conditions where inhibition of amyloid aggregation is necessary, the method comprising administering a composition according to claim 1 as part of a pharmaceutical formulation.

8. The method of claim 7, wherein the conditions are selected from the group consisting of Alzheimer's disease, Hereditary cerebral hemorrhage with amyloidosis, Parkinson's disease, Dementia with Lewy bodies, Multiple system atrophy, Creutzfeldt-Jakob disease, Fatal insomnia, Gerstmann-Straussler-Scheinker disease, Huntington disease, Spongiform encephalopathy, New variant Creutzfeldt-Jakob disease, Kuru, Hereditary sensory and autonomic neuropathy, Pick disease, Progressive supranuclear palsy, Corticobasal degeneration, Frontotemporal dementia, Argyrophilic grain disease, Tangle predominant dementia, Guam Parkinson dementia complex, Frontotemporal lobar degeneration, Chronic traumatic encephalopathy, Ganglioglioma, Meningioangiomatosis, Subacute sclerosing panencephalitis, Lead encephalopathy, Tuberous sclerosis, Hallervorden-Spatz disease, Lipofuscinosis, Familial British dementia, Familial Danish dementia, Light-chain amyloidosis, Heavy-chain amyloidosis, AA amyloidosis, Senile systemic amyloidosis, Familial amyloidotic polyneuropathy, Familial amyloid cardiomyopathy, Leptomeningeal amyloidosis, Dialysis-related amyloidosis, ApoAI amyloidosis, ApoAII amyloidosis, ApoAIV amyloidosis, ApoCII amyloidosis, ApoCIII amyloidosis, Finnish type Familial amyloidosis, Lysozyme amyloidosis, Fibrinogen amyloidosis, Hereditary cerebral hemorrhage with amyloidosis, Type II diabetes, Insulinoma, Medullary carcinoma of the thyroid, Atrial amyloidosis, Pituitary prolactinoma, Injection-localized amyloidosis, Aortic medial amyloidosis, Gelatinous drop-like corneal dystrophy, Calcifying epithelial odontogenic tumors, Pulmonary alveolar proteinosis, Renal amyloidosis, Lichen amyloidosus, Macular amyloidosis, Hypotrichosis simplex of the scalp, type 1 Lattice corneal dystrophy, type 3A Lattice corneal dystrophy, Avellino type Lattice corneal dystrophy, Seminal vesicle amyloidosis, and Prostate cancer.

9. A method for the treatment of disorders mediated by amyloid aggregation, the method comprising administering a composition according to claim 1 as part of a pharmaceutical formulation.

10. The method of claim 9, wherein the disorders are selected from the group consisting of Alzheimer's disease, Hereditary cerebral hemorrhage with amyloidosis, Parkinson's disease, Dementia with Lewy bodies, Multiple system atrophy, Creutzfeldt-Jakob disease, Fatal insomnia, Gerstmann-Straussler-Scheinker disease, Huntington disease, Spongiform encephalopathy, New variant Creutzfeldt-Jakob disease, Kuru, Hereditary sensory and autonomic neuropathy, Pick disease, Progressive supranuclear palsy, Corticobasal degeneration, Frontotemporal dementia, Argyrophilic grain disease, Tangle predominant dementia, Guam Parkinson dementia complex, Frontotemporal lobar degeneration, Chronic traumatic encephalopathy, Ganglioglioma, Meningioangiomatosis, Subacute sclerosing panencephalitis, Lead encephalopathy, Tuberous sclerosis, Hallervorden-Spatz disease, Lipofuscinosis, Familial British dementia, Familial Danish dementia, Light-chain amyloidosis, Heavy-chain amyloidosis, AA amyloidosis, Senile systemic amyloidosis, Familial amyloidotic polyneuropathy, Familial amyloid cardiomyopathy, Leptomeningeal amyloidosis, Dialysis-related amyloidosis, ApoAI amyloidosis, ApoAII amyloidosis, ApoAIV amyloidosis, ApoCII amyloidosis, ApoCIII amyloidosis, Finnish type Familial amyloidosis, Lysozyme amyloidosis, Fibrinogen amyloidosis, Hereditary cerebral hemorrhage with amyloidosis, Type II diabetes, Insulinoma, Medullary carcinoma of the thyroid, Atrial amyloidosis, Pituitary prolactinoma, Injection-localized amyloidosis, Aortic medial amyloidosis, Gelatinous drop-like corneal dystrophy, Calcifying epithelial odontogenic tumors, Pulmonary alveolar proteinosis, Renal amyloidosis, Lichen amyloidosus, Macular amyloidosis, Hypotrichosis simplex of the scalp, type 1 Lattice corneal dystrophy, type 3A Lattice corneal dystrophy, Avellino type Lattice corneal dystrophy, Seminal vesicle amyloidosis, and Prostate cancer.

* * * * *